(12) United States Patent  (10) Patent No.: US 8,157,803 B1
Zirkle, Jr. et al.  (45) Date of Patent: Apr. 17, 2012

(54) BONE FIXATION USING AN INTRAMEDULLARY NAIL INTERLOCKED WITH A BUTTRESS MEMBER

(75) Inventors: Lewis G. Zirkle, Jr., Richland, WA (US); Franklyn D. Faultersack, Kennewick, WA (US); Dule Mehic, Kennewick, WA (US); Richard D. Grizzell, Walla Walla, WA (US)

(73) Assignee: Surgical Implant Generation Network, Richland, WA (US)

( * ) Notice: Subject to any disclaimer, the term of this patent is extended or adjusted under 35 U.S.C. 154(b) by 751 days.

(21) Appl. No.: 12/229,512

(22) Filed: Aug. 21, 2008

Related U.S. Application Data

(60) Provisional application No. 60/957,145, filed on Aug. 21, 2007.

(51) Int. Cl.
*A61B 17/72* (2006.01)
(52) U.S. Cl. .............................. 606/64; 606/65; 606/67
(58) Field of Classification Search ............... 606/62–68
See application file for complete search history.

(56) References Cited

U.S. PATENT DOCUMENTS

| | | | |
|---|---|---|---|
| 2,834,342 A | 5/1958 | Yost | |
| 3,433,220 A | 3/1969 | Zickel | |
| 3,489,143 A | 1/1970 | Halloran | |
| 3,670,724 A * | 6/1972 | Bosacco | 606/64 |
| 3,709,218 A * | 1/1973 | Halloran | 606/64 |
| 4,172,452 A | 10/1979 | Forte | |
| 4,438,762 A | 3/1984 | Kyle | |
| 4,488,543 A | 12/1984 | Tornier | |
| 4,622,959 A | 11/1986 | Marcus | |
| 4,640,271 A * | 2/1987 | Lower | 606/65 |
| 4,733,654 A * | 3/1988 | Marino | 606/64 |
| 4,791,918 A | 12/1988 | Von Hasselbach | |
| 4,794,919 A | 1/1989 | Nilsson | |
| 4,973,332 A | 11/1990 | Kummer | |
| 5,167,663 A | 12/1992 | Brumfield | |
| 5,356,410 A * | 10/1994 | Pennig | 606/62 |
| 5,429,640 A | 7/1995 | Shuler et al. | |
| 5,728,099 A * | 3/1998 | Tellman et al. | 606/65 |
| 6,126,661 A | 10/2000 | Faccioli et al. | |
| 6,706,046 B2 * | 3/2004 | Orbay et al. | 606/62 |
| 6,730,090 B2 | 5/2004 | Orbay et al. | |
| 6,755,862 B2 * | 6/2004 | Keynan | 623/16.11 |
| 7,066,943 B2 | 6/2006 | Zirkle, Jr. | |
| 7,070,601 B2 | 7/2006 | Culbert et al. | |
| 7,135,023 B2 * | 11/2006 | Watkins et al. | 606/65 |
| 7,182,765 B2 | 2/2007 | Roth et al. | |
| 2006/0100623 A1 * | 5/2006 | Pennig | 606/64 |
| 2007/0055248 A1 | 3/2007 | Zlowodski et al. | |
| 2007/0219636 A1 * | 9/2007 | Thakkar | 623/18.11 |
| 2008/0091203 A1 * | 4/2008 | Warburton et al. | 606/62 |

* cited by examiner

*Primary Examiner* — Eduardo C Robert
*Assistant Examiner* — Jerry Cumberledge
(74) *Attorney, Agent, or Firm* — Kolisch Hartwell, PC

(57) ABSTRACT

System, including methods, apparatus, and kits, for fixing a bone using an intramedullary nail interlocked with a buttress member disposed on the bone.

15 Claims, 10 Drawing Sheets

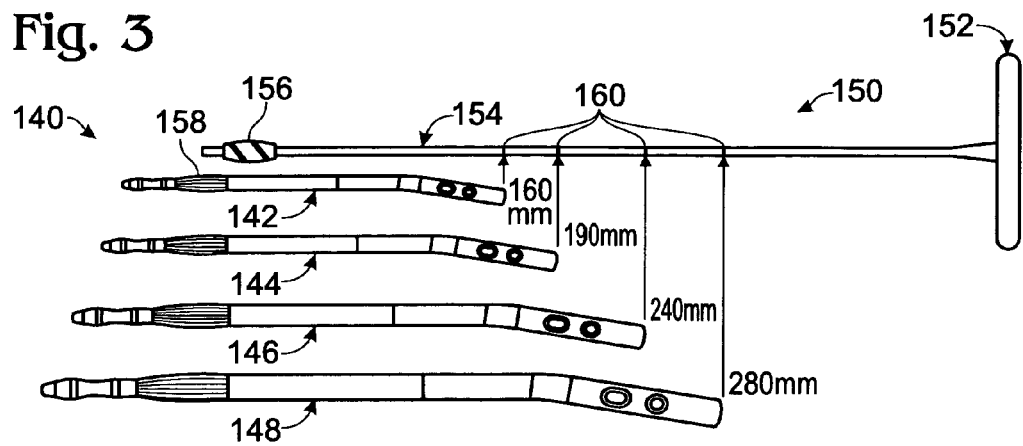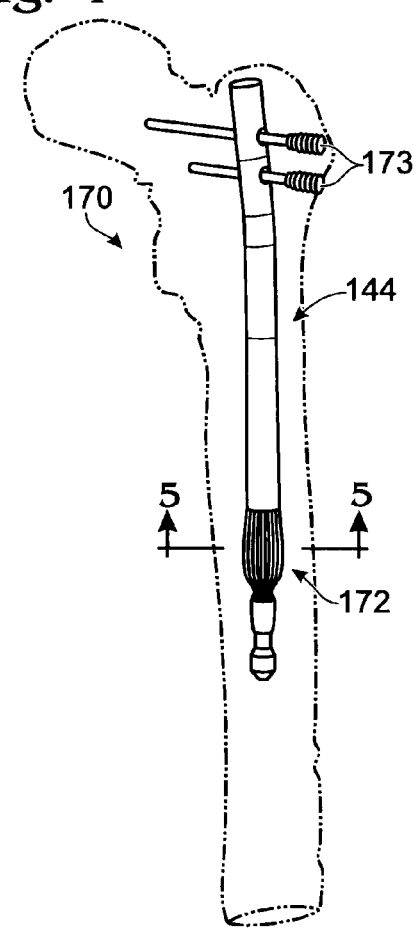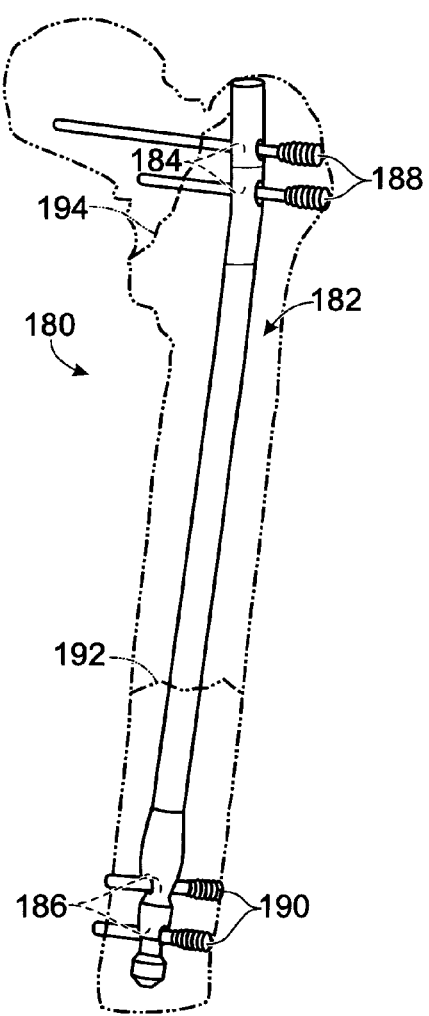

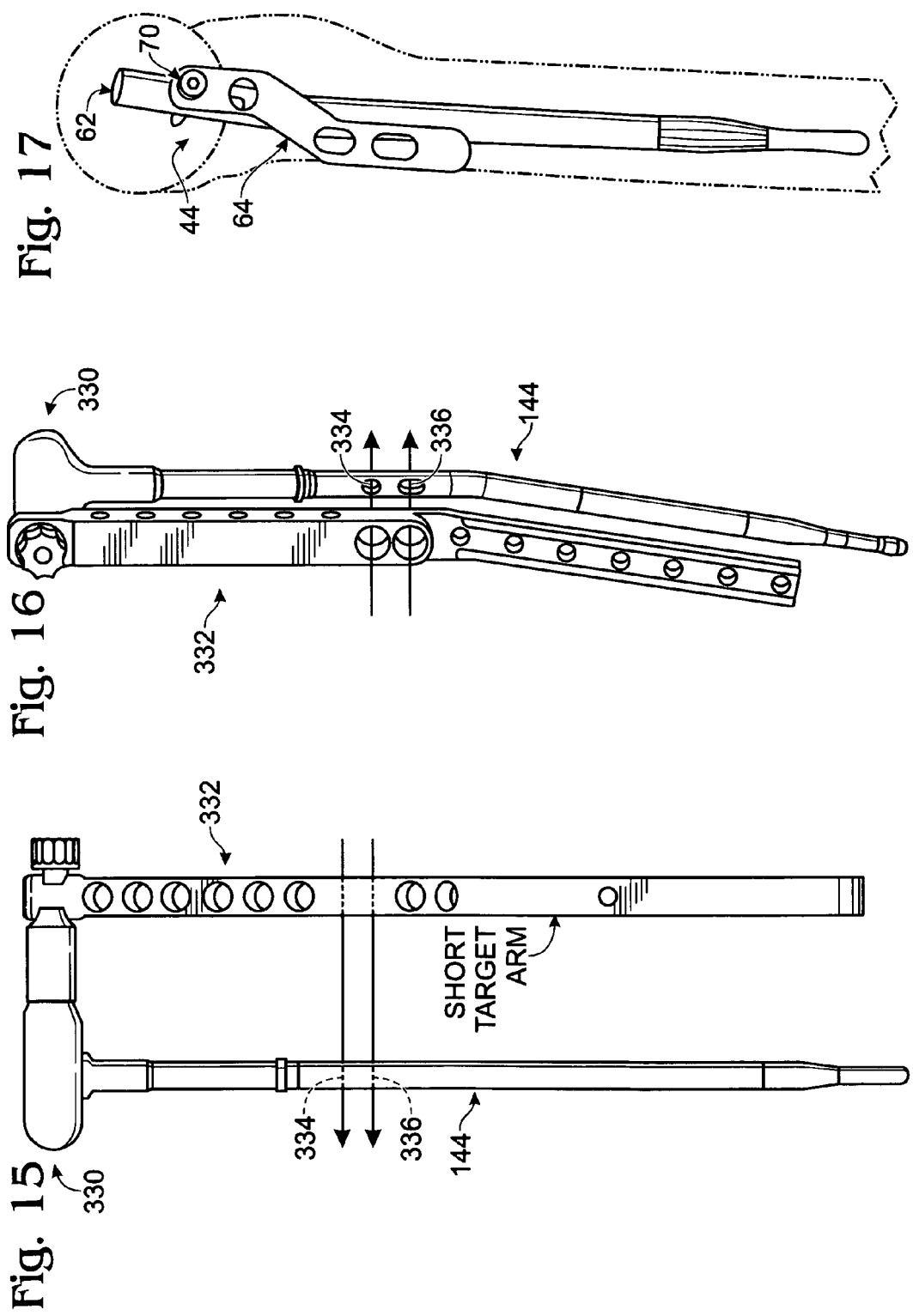

Fig. 24
Fig. 25
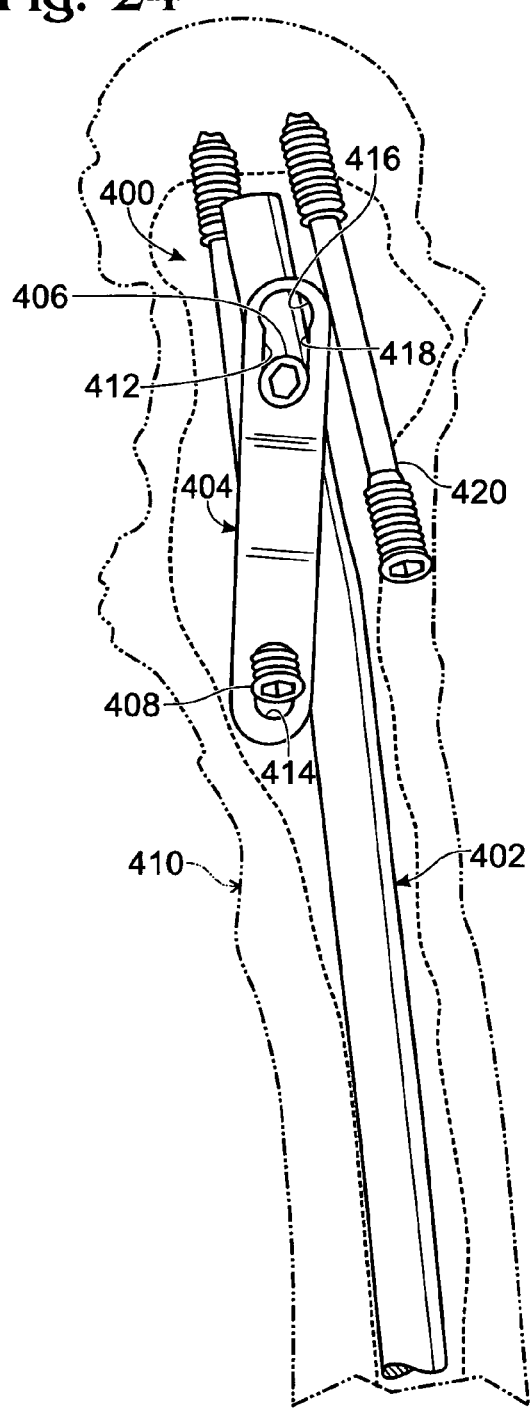
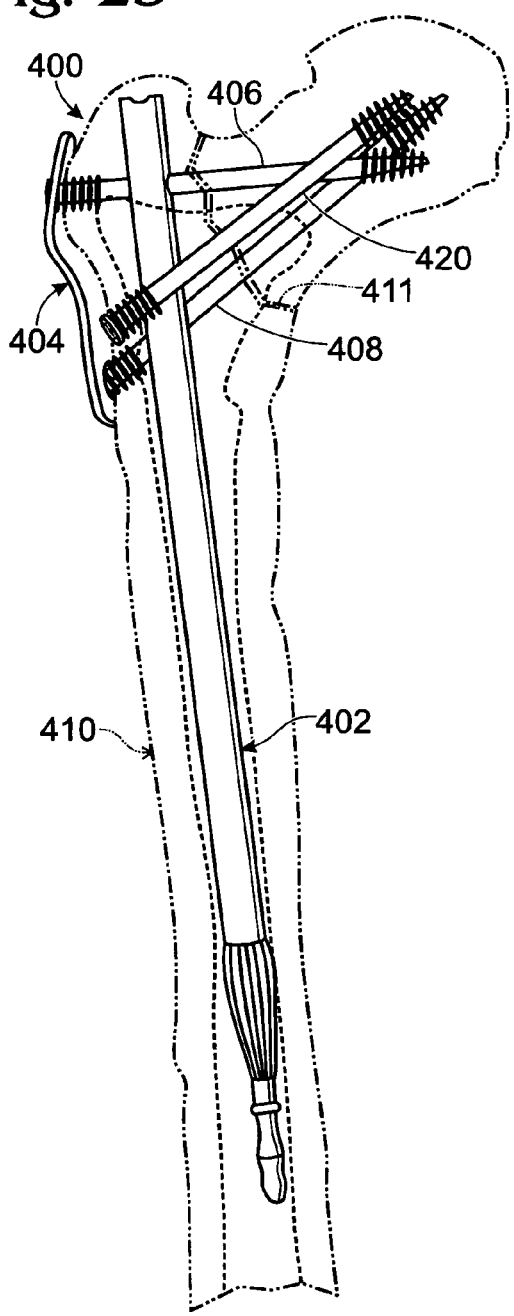

BONE FIXATION USING AN INTRAMEDULLARY NAIL INTERLOCKED WITH A BUTTRESS MEMBER

CROSS-REFERENCE TO PRIORITY APPLICATION

This application is based upon and claims the benefit under 35 U.S.C. §119(e) of U.S. Provisional Patent Application Ser. No. 60/957,145, filed Aug. 21, 2007, which is incorporated herein by reference in its entirety for all purposes.

CROSS-REFERENCE TO RELATED MATERIAL

This application incorporates U.S. Pat. No. 7,066,943 herein by reference in its entirety for all purposes.

BACKGROUND

The femur or thigh bone is the longest, largest, and strongest bone of the body. Proximally, the femur has a spherical head (the femoral head) that articulates with the pelvis to form the hip joint. The femoral head is connected to the body of the femur (the femoral body) by a neck that extends obliquely from the body of the femur, such that the femoral head is disposed medially and superiorly to the femoral body. Distally, the femur forms a pair of femoral condyles that articulate with the tibia to form medial and lateral compartments of the knee joint.

Fractures of the femur may be treated using various procedures, determined in part by the nature of the fracture. Segmental fractures of the femur, that is, two or more fractures in the shaft of the femur that create a fracture-bounded segment, are often fixed with an intramedullary nail disposed longitudinally in the medullary canal of the femur. The nail may be secured to the femur on opposing sides of the fracture-bounded segment using fasteners, such as bone screws, to fix the fractured femur.

In contrast to segmental fractures, fractures near either end of the femur may be more difficult to fix because the attached muscles tend to pull bone fragments in non-longitudinal directions. For example, femoral hip fractures ("pertrochanteric fractures") may extend obliquely and/or longitudinally near and/or through the greater and/or lesser trochanters of the proximal femur, to separate the femoral head from the femoral body. Many pertrochanteric fractures are also characterized as intertrochanteric fractures that involve one ("stable" intertrochanteric fractures) or both ("unstable" intertrochanteric fractures) trochanters of the femur. Hip fractures are a common orthopedic injury. For example, in the United States, 250,000 hip fractures occur each year. This number may double or triple by the year 2050.

Surgical installation of an orthopedic implant for internal fixation is the treatment of choice for virtually all hip fractures. For example, a large screw coupled obliquely to a bone plate (termed a sliding or compression hip screw) has been used for years to stabilize intertrochanteric fractures. However, there is dissatisfaction with the sliding hip screw because of the loss of reduction that can occur and also because of the extent of soft tissue dissection necessary to install the device.

An increasingly popular, alternative approach to fixation of intertrochanteric hip fractures involves an intramedullary nail coupled to a lag screw. However, in many cases the outcome is unsatisfactory. For example, the lag screw may protrude laterally from the femoral shaft during fracture settling. In addition, a large hole is created in the greater trochanter for receiving the lag screw, which may damage insertion of the abductor muscles necessary for proper hip function. Furthermore, lag screws may exhibit a Z-effect phenomenon, in which the lag screws migrate in opposite directions during physiologic loading. The Z-effect phenomenon may be most common with nail-based fixation devices that incorporate a lag screw sliding within a barrel.

More effective and/or less expensive methods and devices for fixing pertrochanteric fractures and other fractures near the end of the femur are needed. The methods and devices should sufficiently stabilize the fractured femur to limit collapse of pertrochanteric fractures that extend obliquely and/or longitudinally.

SUMMARY

The present disclosure provides a system, including methods, apparatus, and kits, for fixing a bone using an intramedullary nail interlocked with a buttress member disposed on the bone.

BRIEF DESCRIPTION OF THE DRAWINGS

FIG. 3 is a side view of another set of fin nails aligned with an exemplary reamer of the fixation systems to indicate a suitable depth of reaming of bone in relation to a finned region of each nail, in accordance aspects of the present disclosure.

FIG. 4 is a view of a fractured left femur being fixed with one of the intramedullary fin nails of FIG. 3 and without a bone plate, in accordance with aspects of the present disclosure.

FIG. 6 is a view of a fractured left femur being fixed with another exemplary intramedullary nail that may be employed by the fixation systems of the present disclosure.

FIG. 15 is a view of the fin nail of FIG. 14 coupled to a handle and a targeting guide in the absence of bone, in accordance with aspects of present disclosure.

FIG. 16 is a view of the fin nail, handle, and targeting guide of FIG. 15, taken approximately perpendicular to the view of FIG. 15.

FIG. 17 is a view of a fractured femur taken at an intermediate stage of an exemplary method of fixing bone with the fixation device of FIG. 1, in accordance with aspects of the present disclosure.

FIG. 24 is a lateral view of a fractured femur being fixed proximally with another exemplary fixation device that includes an intramedullary nail and a plate, with the bone plate serving as an external buttress member, and with the nail and plate separated by bone and interlocked by a threaded fastener disposed in the femur, in accordance with aspects of the present disclosure.

FIG. 25 is an anterior view of the femur and exemplary fixation device of FIG. 24.

DETAILED DESCRIPTION

Figure 2:
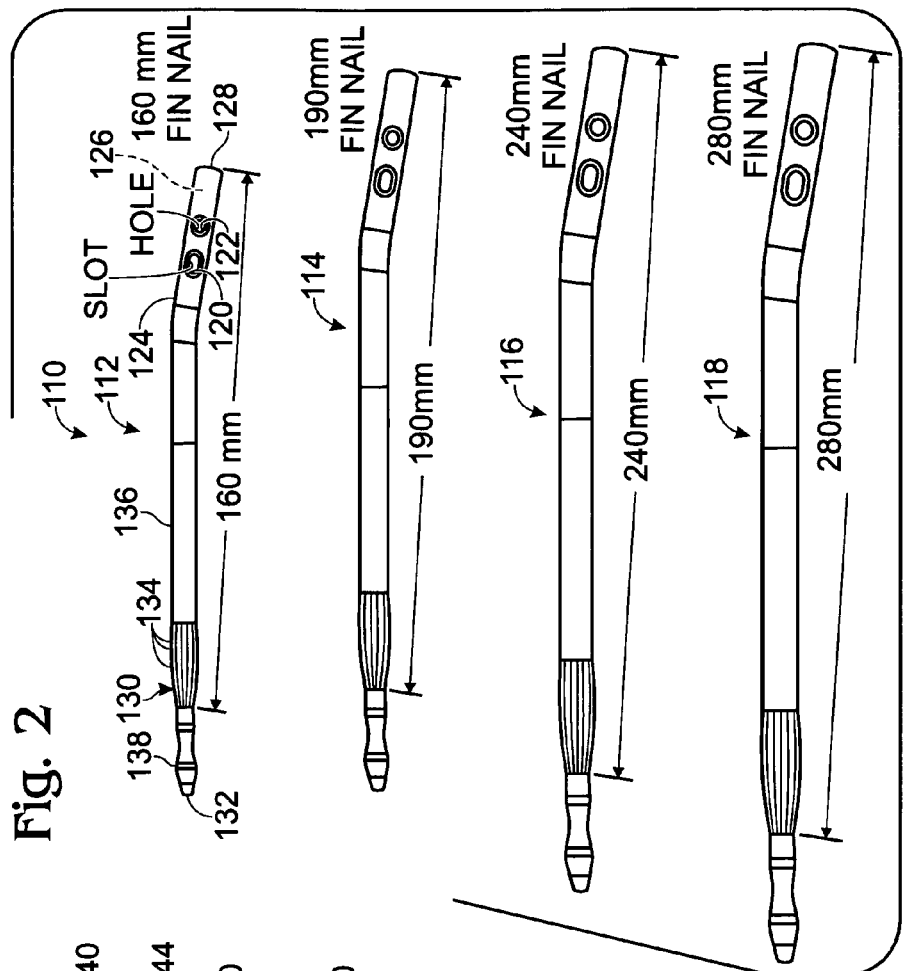
FIG. 2 is a side view of a set of exemplary, intramedullary "fin" nails that may be employed by the fixation systems of the present disclosure.

The present disclosure provides a system, including methods, apparatus, and kits, for fixing a bone using an intramedullary nail interlocked with a buttress member disposed on the bone.

The system may provide a fixation device for fixing a long bone, such as a femur, with one or more discontinuities, such as one or more fractures in a proximal or distal end region of the femur. The fixation device (or a method of fixing bone) may include (or use) an intramedullary nail (a "nail"), a buttress member (e.g., a bone plate and/or a rod), and a plurality of fasteners (e.g., threaded fasteners such as bone screws).

The system may provide substantially improved stabilization of oblique and longitudinal pertrochanteric fractures. In particular, the use of an intramedullary nail in the femur, an external (on-bone) buttress member on the femur, a fastener that interlocks the nail with the buttress member (and with the head/neck of the femur), and another fastener that interlocks the buttress member with the head/neck of the femur provides a very stable construct that resists loss of fracture reduction.

The intramedullary nail may be configured for placement longitudinally into a medullary canal of the bone. The intramedullary nail may include a leading section and a trailing section that enter the bone in that order. The trailing section may define one or more transverse apertures that extend transversely into and/or through the trailing section. The leading section also may define one or more transverse apertures. Alternatively, or in addition, the nail may be a fin nail with a leading section that includes one or more generally longitudinal fins to form a finned region that engages bone to restrict movement of the nail (such as longitudinal and/or turning motion). The use of a fin nail may simplify installation of the fixation device by obviating placement of fasteners for anchoring the leading section of the nail.

The buttress member may be configured for placement adjacent an exterior surface region of the bone. For example, the buttress member may be configured such that that the buttress member, when disposed on the bone, is not in contact with the nail. In particular, the buttress member may be spaced from the nail by an interposed portion of the bone and may not extend as far along bone as the trailing end and/or the leading end of the nail. The buttress member may include first and second anchor portions, each respectively defining one or more first openings and one or more second openings. The one or more first openings may be disposed proximally in the buttress member and may be configured to be aligned with (i.e., be co-axial with) the one or more transverse apertures of the trailing section of the nail. The one or more second openings may be disposed more distally in the buttress member. The first openings and/or the second openings may be oblong or circular, among others.

Each second opening of the buttress member may be defined by a second anchor portion that is coupled to the first anchor portion by a movable joint. The buttress member may have only one or may have two or more discrete second anchor portions that are movable with respect to the first anchor portion. In particular, the second anchor portion may have an adjustable configuration in which the second anchor portion is permitted to slide along (axially) and/or about a long axis defined by the first anchor portion. In some examples, the second anchor portion may include a loop element that defines a distal aperture and that pivots about a transverse axis defined by the first anchor portion. In the adjustable configuration, the second anchor portion may be positioned to provide a customized spacing and angular disposition of the first and second (e.g., proximal and distal) openings of the buttress member, according to the particular anatomy and fracture configuration of a fracture patient to be treated. Furthermore, in the adjustable configuration the second anchor portion may be positioned for placement either anterior or posterior of the first anchor portion on the femur. The second anchor portion also may have a locked configuration in which sliding motion of the second anchor portion along and/or about the long axis of the first anchor portion is restricted. The locked configuration may be imposed by a locking member, such as a lock screw, which may be adjustably engaged with the first (and/or second) anchor portion. The locked configuration may or may not restrict pivotal motion of the loop element about an axis that is transverse to the long axis. In some embodiments, the first anchor portion may include an elongate body having a rod section connected longitudinally to a head section defining at least one proximal opening. The second anchor portion may include a carriage assembly that slides on the rod section. The second anchor portion may project laterally of (to a side of) the first anchor portion, such as projecting laterally to the rod portion to define a distal opening of the buttress member.

The buttress member may have any other suitable features. In some embodiments, at least one of the openings of the buttress member may have an at least two-part structure, with a receiver region of relatively larger width disposed adjacent to a retainer region of relatively smaller width. In some embodiments, the first anchor portion of the buttress member may be elevated with respect to the second anchor portion of the buttress member and/or the first and second anchor portions may be offset laterally from one another. In some embodiments, the buttress member may be contoured according to a contour of the exterior surface region of the bone.

The fasteners may be configured to interlock the buttress member with the nail and with bone by placement into the bone. The term "interlock," as used herein, means that the motion of one element is constrained by another element. The fasteners may include one or more first fasteners that, when the fixation device is installed fully, extend at least between the one or more first openings of the buttress member and the one or more transverse apertures of the nail. The first fasteners may extend only into or also through the first openings and/or transverse apertures. Furthermore, the first fasteners may be locking with respect to the buttress member and/or the nail or may be nonlocking with respect to both. One or more (or all) of the first fasteners may or may not span a discontinuity in the bone. At least one (or all) of the first fasteners may be placed into bone with the first openings of the buttress member co-axial with the transverse apertures of the nail, such that the first fasteners travel through the first openings before they enter the transverse apertures. Alternatively, at least one (or all) of the first fasteners may be placed into bone and at least one (or all) of the transverse apertures of the nail before the at least one first fastener is placed into a first opening of the buttress member. In other words, the buttress member may receive a proximal or head region of a first fastener with the first fastener already disposed in bone, but not necessarily fully advanced into bone. The fasteners also may include one or more second fasteners that, when installed, extend into and/or through the one or more second openings of the buttress member, into the bone, and to one side of the nail (that is, extending past the nail without intersecting the nail). For example, the one or more second openings of the buttress member may be disposed anteriorly or posteriorly in the bone such that the one or more second fasteners extend in a corresponding relative disposition to the nail. The second fasteners may be oriented obliquely to a long axis defined by the nail, the bone plate, and/or the bone, and may extend generally toward a trailing end of the nail (e.g., generally toward the proximal end of the femur). Furthermore, the second fasteners may extend across a fracture to engage a peripheral fragment, such as a fragment of the femur including the femoral head. Accordingly, both the first and second fasteners may extend into the head/neck of the femur. In some embodiments, the second fasteners (and/or the first fasteners) may be configured to compress bone as the fasteners are advanced. For example, each fastener may include a nonuniform pitch, such as with a smaller trailing pitch, or may be configured as a lag screw with a shaft that is only threaded distally (and nonthreaded proximally).

Figure 1:
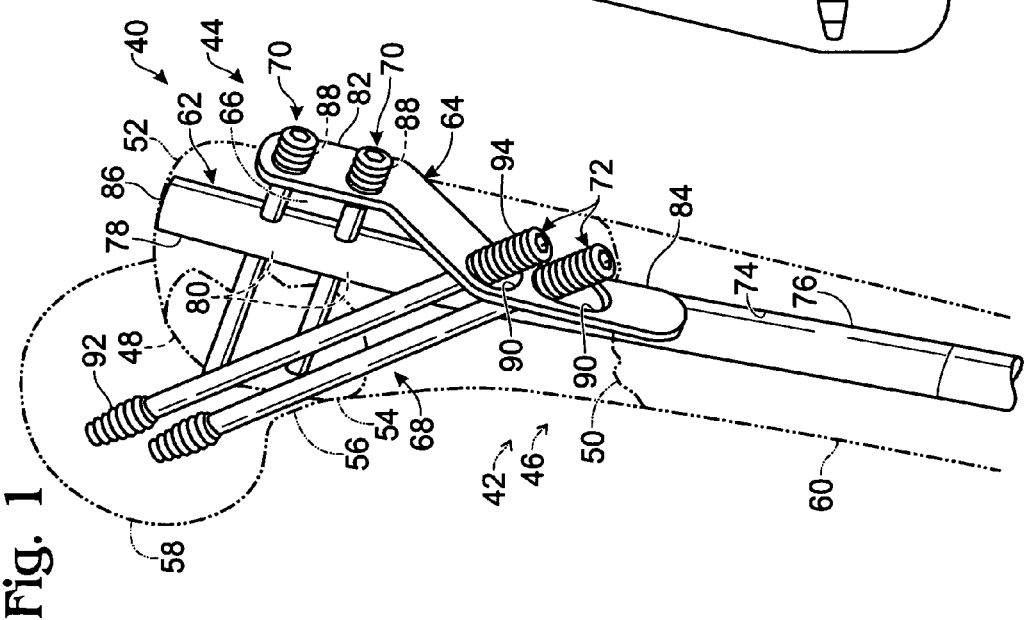
FIG. 1 is a view of a fractured left femur being fixed proximally with an exemplary fixation device that includes an intramedullary nail and a bone plate, which serves as an external (on-bone) buttress member, with the nail and bone plate separated by bone and interlocked by a threaded fastener disposed in the femur, in accordance with aspects of the present disclosure.

FIG. 1 shows selected components of an exemplary fixation system 40 fixing a bone 42 using a fixation device 44 provided by the system. Here, bone 42 is a femur 46 that has sustained a pertrochanteric fracture 48 and a more central fracture(s) 50 (e.g., a single transverse fracture of the shaft, a segmental fracture, and/or a subtrochanteric fracture) of the proximal femur. Pertrochanteric fracture 48, if an intertrochanteric fracture, involves greater trochanter 52 and/or lesser trochanter 54 of the proximal femur. In the present illustration, pertrochanteric fracture 48 is generally medial to the trochanters, extending through a neck 56 of the proximal femur to separate femoral head 58 from femoral body 60. In other examples, the system of the present disclosure may provide a fixation device for, and/or install a fixation device in, any suitable long bone of the body, such as a leg bone (e.g., a distal or proximal end region of a femur, a tibia, or a fibula) or an arm bone (e.g., a distal or proximal end region of a humerus, a radius, or an ulna), among others.

Fixation device 44 may include an intramedullary nail 62 and at least one external buttress member, such as bone plate 64 placed onto an exterior surface region femur 46. Nail 62 and bone plate 64 may be separated by a region of the bone (e.g., lateral cortex 66) and coupled by one or more fasteners 68, such as transverse fasteners 70. Fasteners 68 also may include one or more oblique fasteners 72 that span a fracture (e.g., here, pertrochanteric fracture 48) and couple to bone plate 64.

Nail 62 may be configured to be disposed longitudinally in a medullary canal 74 of bone 42. The nail may include a leading section 76 that enters the medullary canal first and a trailing section 78 that follows the leading section into bone. For example, here, the leading and trailing sections of the nail have entered femur 46 through a hole in greater trochanter 52.

The leading and/or trailing sections of the nail each may define one or more transverse apertures. For example, trailing section 78 may define at least two transverse apertures 80. Each transverse aperture may be structured as a through-hole, as shown here, or as a blind hole, among others. The transverse apertures may be sized to receive a shank of transverse fasteners 70. In some embodiments, the nail may define one or more transverse apertures configured to receive one or more oblique fasteners 72, to permit the oblique fastener to extend through the nail, rather than to the side of the nail as shown here. Further aspects of nails that may be suitable are described elsewhere in the present disclosure, such as in Section I.

Bone plate 64 (or another buttress member) may be configured to be disposed adjacent an exterior surface region of bone 42. The bone plate (or buttress member) thus may be shaped in general correspondence with a contour of the exterior surface region, such that the bone plate follows the exterior surface region and may maintain a low profile on the bone. The bone plate may include a first plate portion 82 and a second plate portion 84, here, arranged as a proximal plate portion and distal plate portion on the bone. In any event, the first and second plate portions may be arranged generally longitudinally along the long axis of the bone plate.

First plate portion 82 may be configured to be disposed closer to a trailing end 86 of nail 62. The first plate portion may define one or more first openings 88 for coupling bone plate 64 to nail 62 via transverse fasteners 70. First openings 88 thus may be spaced in correspondence with transverse apertures 80 of the nail, such as having about the same spacing from each other as the transverse apertures. The first openings may be sized to receive the respective shanks and/or heads of transverse fasteners 70. In some embodiments, the first openings may be sized to restrict and/or permit passage of the heads of transverse fasteners 70 through the first openings.

Second plate portion 84 may be configured to be disposed closer to a leading end of nail 62. The second plate portion may be offset from the first plate portion. For example, the second plate portion may be offset along the z-axis of the plate, such that the first (or second) plate portion is elevated with respect to the second (or first) plate portion, to maintain a lower profile of the bone plate on bone. Alternatively, or in addition, second plate portion 84 may be offset laterally (with respect to the width axis of the plate). The second plate portion may define any suitable number of second openings 90. The second openings may define oblique axes along which oblique fasteners 72 may be placed into bone, generally toward trailing end 86 of the nail. Here, for example, oblique fasteners 72 extend anteriorly to nail 62, through and generally perpendicular to pertrochanteric fracture 48, and into head 58 of the femur. One or more of transverse fasteners 70 also may have a length sufficient to span pertrochanteric fracture 48 (or another fracture of the bone). Further aspects of bone plates that may be suitable are described elsewhere in the present disclosure, such as in Sections II and VII.

Each of fasteners 68 may include at least one threaded region for engaging bone, nail 62, and/or bone plate 64. For example, here, each fastener 68 has a distal threaded region 92. In some embodiments, fastener 68 may include a proximal threaded region 94 that is spaced from the distal threaded region. The proximal threaded region may be formed on a head of the fastener. Further aspects of fasteners that may be suitable are described elsewhere in the present disclosure, such as in Section III.

The systems of the present disclosure may provide substantial advantages for bone fixation. Exemplary advantages that may be provided by selected embodiments are numbered in the remainder of this paragraph, although the advantages may be provided in any suitable combination, with each advantage being optional. (1) The fixation device may employ a nail with a smaller diameter than prior art devices, thereby causing less damage to the abductor muscles. (2) The fixation device may include one or more first screws extending through the nail at about 90° from the axis of the nail and one or more second screws that do not intersect the nail and that extend at about 125° from the axis of the nail. This arrangement of coupled screws extending into the femoral neck and head may provide a stronger construct, which may allow earlier weight-bearing. (3) The fixation device may include one or more screws with a thread formed on the head of each screw, which may decrease the possibility of migration of the screws. (4) The fixation device may employ longer oblique screws, which may be lag screws designed to provide compression along an axis perpendicular to a plane defined by the fracture and thus compression of the fracture. Seventy percent of the stability of a hip fracture is inherent in the reduction. (5) The fixation device may include a plate- or rod-based buttress member (disposed on bone and under soft tissue) that ties the device together to provide increased stability. (6) The design of the fixation device may allow installation without real-time X-ray imaging, such as without C-arm image intensification. (7) The same fixation device and/or selected components thereof may be used for pertrochanteric and/or segmental fractures. (8) The fixation device may include a fin nail that is secured distally by engagement with bone and without fasteners. By not using distal fasteners to secure the nail, the chance of a stress fracture in the femoral shaft may be decreased and/or installation may be performed more quickly and with less injury to soft tissue. (9) Occasionally, at the time of surgery for a segmental fracture, a hip fracture may be discovered, and/or may be caused by, installation of an intramedullary nail into the femur. A buttress member and oblique screws then can be used with the nail that is already implanted to fix the newly discovered fracture of the hip. (10) The fixation device may be installed without creating a large hole in the lateral cortex of the femur, in contrast to when one large lag screw is used.

The following sections describe further aspects of the present disclosure, including, among others, (I) intramedullary nails, (II) buttress members, (III) fasteners, (IV) composition of system components, (V) methods of fixing bones using a nail coupled to a buttress member, (VI) systems/kits for fixing bone using a nail coupled to a buttress member, and (VII) examples.

I. INTRAMEDULLARY NAILS

An intramedullary nail (a "nail"), as used herein, generally comprises any orthopedic rod for placement longitudinally into a medullary canal of a bone to reinforce and stabilize the bone. The nail may have any suitable shape, size, and structural features.

The nail may be shaped as a rod. The rod may have a directionality for placement into bone, with a longitudinal asymmetry defining opposing leading and trailing ends. In some embodiments, rod may be narrower toward the leading end to define the directionality of placement. The rod may be linear or may be nonlinear. If nonlinear, the rod may have a bent configuration provided by one or more angular or arcuate bends. The rod may have any suitable cross-sectional shape, including circular, rosette, stellate, polygonal, and/or the like. The cross-sectional shape may be the same along the length of the rod or may be different at distinct longitudinal positions. In some embodiments, the cross-sectional shape of a least a longitudinal section of the rod may be determined by one or more generally longitudinal ridges (fins) and/or grooves (flutes).

The nail may have any suitable length and diameter. The length may correspond to any fraction of the length of a target bone, such as less than or greater than about one-half, or less than or greater than about one-fourth, among others. The length may be fixed or may be adjustable, such as by a telescoping mechanism or addition of (or removal of) one or more extension modules to (or from) the nail. The diameter of the nail may correspond to the diameter of a medullary canal of a target bone, before or after reaming the medullary canal to increase its diameter. In some embodiments, the diameter of the nail may decrease substantially near a leading end of the nail in order to produce an elongate tip.

The nail may have any suitable apertures. For example, the nail may define one or more transverse apertures in a trailing section and/or a leading section of the nail. In some embodiments, the trailing section and the leading section may be a respective trailing half and leading half of the rod as determined by length. Each transverse aperture may have any suitable shape with respect to the axis of the aperture, such as circular to provide a cylindrical aperture, or oblong to provide an aperture that is elongated along the long axis of the nail or transverse to the long axis, among others. Each transverse aperture may extend into and/or through the nail along any suitable axis. The axis may be substantially orthogonal to the long axis of the rod or may be oblique to the long axis. The axes along which apertures extend may be parallel or angularly offset with respect to each other about the long axis of the nail and/or about a transverse axis (or axes) of the nail. In some embodiments, the nail may define at least one longitudinal aperture that extends lengthwise into and/or through the nail. Accordingly, the nail may be cannulated. Each aperture may define a locking structure, such as an internal thread, for locking engagement of a fastener, a handle, a targeting guide, a positioning jig, and/or the like.

The nail may have any other structural aspects. The nail may be a unitary structure, with no separable components, or may be formed of two or more components. If unitary, the nail may be a monolithic structure or may be formed of two or more permanently joined structures/components. The nail may be substantially rigid or flexible.

FIG. 2 shows a set 110 of exemplary, intramedullary "fin" nails 112-118 that may be employed by the fixation systems to provide fixation devices of different length. Each fin nail may include a pair of transverse apertures 120, 122 defined in a trailing section 124 of the nail. The transverse apertures may extend along and define parallel axes. One (or both) of the apertures may be a through-hole structured as a slot with an oblong shape oriented substantially parallel to the long axis of the rod. Furthermore, one (or both) of the apertures may be a cylindrical through-hole. For example, here, leading or distal aperture 120 is a slot and trailing or proximal aperture 122 is a cylindrical through-hole. The fin nail also may define a longitudinal opening 126 extending into the nail from a trailing end 128 of the nail, to permit the nail to be locked to a tool (e.g., a handle/targeting guide/positioning jig). The longitudinal opening may, for example, include an internal thread for threaded engagement with the tool.

The terms "proximal" and "distal," as used herein to describe a fixation device or components/component portions thereof, are with respect to an end/exterior surface of a bone in/on which the device/components/portions are being installed and/or with respect to a practitioner installing the device or components/component portions, with proximal meaning closer to the end/exterior surface of the bone and/or to the practitioner and distal meaning farther from the end/exterior surface of the bone and/or from the practitioner.

The fin nail may include a finned region 130 disposed near a leading end 132 of the nail. Finned region 130 may include at least one, and generally a plurality, of fins 134 that extend longitudinally along the nail. The finned region may have a maximum diameter that is greater than the average diameter of the nail rearward of the thinned region in a trailing body 136 of the nail. The nail may form a tip 138 forward of the finned region. The tip may be elongate, with a length that is about the same as, substantially less than, or substantially greater than the length of the finned region. The tip may have a diameter that is substantially less than the diameter of trailing body 136, or the diameter may be about the same.

FIG. 3 shows another set 140 of fin nails 142-148 aligned with an exemplary reamer 150 that may be employed by the systems of the present disclosure. Here, fin nails 142-148 have respective trailing bodies of the same diameter, in contrast to set 110 of FIG. 2 where the diameter of each nail increases with nail length. Reamer 150 may include a handle portion 152 and an elongate stem portion 154 extending from the handle portion. Stem portion 154 may include a reamer structure 156 with one or more blades for enlarging a medullary canal as the reamer is turned. The reamer structure may have a diameter corresponding to a finned region 158 of the nail, to ream the medullary canal for advancement of the finned region up to a position where the finned region is forced into and seats in a narrower region of the medullary canal. The stem portion also may include reference marks 160 indicating how far the reamer should be advanced into bone for each fin nail. In particular, each reference mark may correspond to a distance from a forward end of reamer structure 156 that is equal to the length of a corresponding nail from the trailing end of the finned region to the trailing end of the nail, as shown in FIG. 3.

FIG. 4 shows fin nail 144 of FIG. 3 fixing a fractured femur 170 without a bone plate. A finned region 172 of the nail may engage the wall of the medullary canal distally, to restrict rotation of the nail about its long axis and also to restrict longitudinal motion of the nail. Accordingly, the nail may be held in place by proximal bone screws 173 and finned region 172 without the use of distal bone screws.

Figure 5:
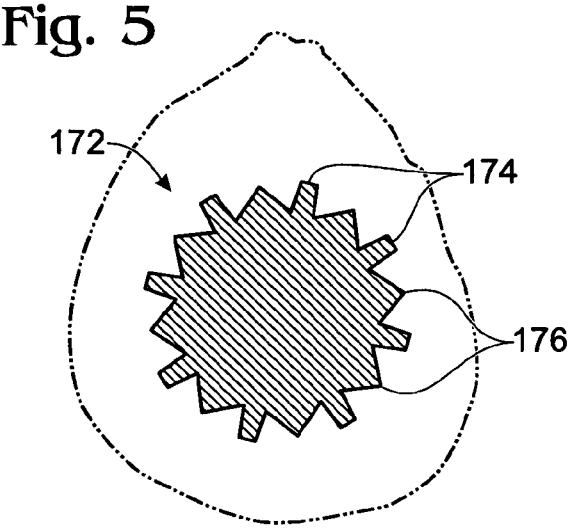
FIG. 5 is a sectional view of the left femur and fin nail of FIG. 4, taken generally along line 5-5 of FIG. 4 through a finned region of the nail.

FIG. 5 shows a sectional view of the left femur and fin nail of FIG. 4, taken generally along line 5-5 of FIG. 4 through finned region 172. The finned region may include fins of different size, such as narrower fins 174 and broader fins 176. Each fin may define a blunt edge and/or a sharp edge.

FIG. 6 shows a fractured left femur 180 being fixed with another exemplary intramedullary nail 182. The nail may define proximal apertures 184 and distal apertures 186 for receiving corresponding proximal and distal bone screws 188, 190 that secure the nail to femur 180. The nail may be suitable for fixation of a shaft fracture 192 and/or a pertrochanteric fracture 194. Fracture 194 may be spanned by one or both proximal bone screws 188.

Nail 182 may be coupled to a bone plate, as described herein, to facilitate placement of oblique fasteners and to provide more stable fixation of femur 180 (or another bone). A nail with proximal and distal apertures (e.g., rather than with proximal apertures and a distal finned region) may be more suitable if the nail extends substantially past the narrowest point of the medullary canal. For example, here, shaft fracture 192 is disposed at about the narrowest point of the medullary canal and the nail extends past the narrowest point to a wider region of the medullary canal, where engagement of bone by a finned region may be less effective. In the case of the proximal femur, a fin nail may be suitable if the most distal fracture is within about the most proximal one-third to one-fourth of the femur.

II. BUTTRESS MEMBERS

A buttress member, as used herein, generally comprises any plate- and/or rod-shaped member of a fixation device configured for orthopedic use, and more specifically, a plate-shaped member (e.g., a bone plate) and/or rod-shaped member for placement onto and/or adjacent an exterior surface region of bone. The buttress member may be configured (i.e., shaped, sized, and/or composed) for internal use, that is, for placement under skin and/or between soft tissue and bone. The buttress member may have any suitable shape, size, and structural features consistent with its intended purpose.

The buttress member may be shaped to be received on a target surface region of a bone and to generally follow the target surface region as the buttress member extends lengthwise (and, optionally, widthwise), to reduce the profile of the buttress member above bone. Accordingly, the buttress member may bend as it extends lengthwise, in correspondence with the target surface region of bone. The buttress member may be contoured according to a general target surface region of bone substantially during manufacture of the buttress member, that is, before the buttress member is supplied to and used by a practitioner. Alternatively, or in addition, the buttress member may be shaped peri-operatively (e.g., by bending in an operating room according to a specific target surface region of a fracture patient).

The buttress member may or may not have bilateral symmetry crosswise to the long axis of the buttress member. For example, with bilateral symmetry, the same buttress member may be used on the same corresponding bone regions on the left and right side of the body. Alternatively, without bilateral symmetry, distinct left and right buttress members (e.g., with mirror-image symmetry) may be provided for use on corresponding bone regions on the left and right side of the body. In some embodiments, the same bone plate without bilateral symmetry may be used on partially corresponding bone regions on either the left side or the right side of the body, such as for placement of an oblique fastener anteriorly to a nail on the left side or posteriorly to a nail on the right side (or vice versa).

A bone plate used as the buttress member may have an inner surface (a bone-facing and/or bone-contacting surface) with any suitable shape. For example, the inner surface may be shaped generally complementary, lengthwise and/or widthwise, to the target surface region of bone. The inner surface thus may be concave, linear, and/or convex lengthwise and/or widthwise, to provide regions of the inner surface that are substantially nonplanar or planar. The inner surface may include any suitable variations in surface structure in the form of a projection(s) and/or a recess(es). Exemplary surface structure may include one or more undulations, that is, ridges and/or knobs to engage bone and elevate the remainder of the inner surface of the bone plate above bone, to, for example, improve blood flow and/or reduce soft tissue damage under the bone plate. Other exemplary surface structure may include one or more prongs to engage bone and restrict slippage of the bone plate along the bone surface. The inner surface may have a smooth or rough texture.

The bone plate may have an outer surface (a bone-opposing surface) with any suitable shape. For example, the outer surface may be shaped generally complementary to the inner surface of the bone plate or may have a substantially distinct shape. The perimeter of the outer surface may be rounded or otherwise shaped to provide a tapered perimeter of the bone plate, which may reduce injury to overlying soft tissue. The outer surface also or alternatively may define a recessed region in the form of a countersink structure around one or more (or all) openings of the bone plate, such as to provide a structure for at least partially receiving a head of a fastener, to reduce protrusion of the head above the outer surface of the bone plate.

The buttress member may have any suitable size. The length of the buttress member may be substantially less than, about the same as, or substantially greater than the length of the intramedullary nail to which the buttress member is coupled.

The buttress member may define any suitable openings. The openings may be through-openings that extend to both the inner surface and the outer surface of the buttress member. Furthermore, each through-opening may be an internal opening, that is, an opening completely bounded circumferentially, or an external opening (a perimeter opening), that is, an opening forming a portion of the perimeter of the buttress member.

Each internal opening may have any suitable shape in a plane defined by the buttress member, such as circular or oblong, among others. If oblong, the internal opening may be elongate in a direction generally parallel, orthogonal, or oblique to the long axis of the buttress member. Furthermore, if oblong, the internal opening may have opposing walls that are only concave (and/or linear) with respect to the long axis of the internal opening. Alternatively, one or both of the opposing walls may project inward at one or more positions along the long axis such that the internal opening is narrowed at one or more positions intermediate the opposing ends of the internal opening. As a result, the internal opening may have a multi-part structure, such as an internal opening with a receiver region and a retainer region (see below). The buttress member may have any suitable number of internal openings, such as one, two, or more internal openings formed in two or more generally longitudinally arranged portions of the buttress member.

Each opening of the buttress member may be locking or nonlocking. If locking, the opening may be manufactured with an internal thread, or a wall/lip of the opening may be configured to be deformed by a fastener thread during fastener placement, to lock the fastener to the bone plate. Accordingly, the wall/lip of the opening (and/or the buttress member) may be formed of material that is soft enough to be deformed by the fastener thread. With a deformable opening, the fastener may be locked to the buttress member over a range of angles (e.g., about 10, 20, 30, or 40 degrees) permitted by the geometry of the opening.

The buttress member may be formed of any suitable number of components. For example, the buttress member may be unitary, with or without a monolithic structure. Alternatively, the buttress member may be formed of two or more discrete pieces.

Figure 7:
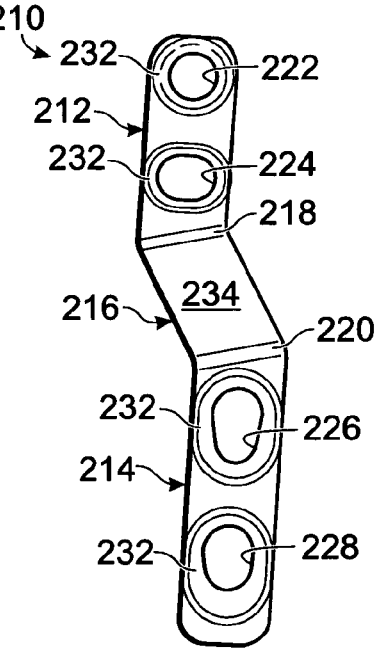
FIG. 7 is a bottom view of an exemplary bone plate that may be employed by the systems of the present disclosure.
Figure 8:
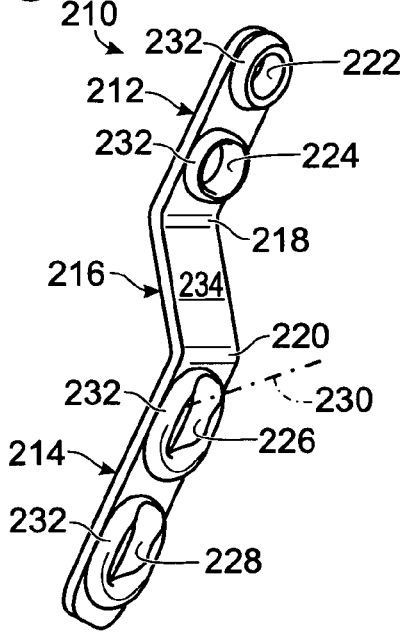
FIG. 8 is a bottom side view of the exemplary bone plate of FIG. 7.

FIGS. 7 and 8 show distinct bottom views an exemplary bone plate 210 that may be included in fixation devices of the systems of the present disclosure. Bone plate 210 may include a first plate portion 212 and a second plate portion 214 connected longitudinally by a bridge portion 216. Each of the plate portions may be generally planar (or generally nonplanar), with bent regions 218, 220 disposing adjacent plate portions at distinct angles. The bent regions may form relatively sharp angular transitions, as shown here, or may be substantially coextensive with the plate portions, to form more smoothly contoured, arcuate transitions between/within the plate portions. First and second plate portions 212, 214 may be substantially parallel to each other or may be oblique to each other with respect to the long axis and/or with respect to a width axis of the bone plate. In addition, the first plate portion may be elevated above the second plate portion, as shown here, or vice versa, among others. Furthermore, the first plate portion and a second plate portion may be laterally offset with respect to each other.

First plate portion 212 may define first openings 222, 224 for coupling the bone plate to a nail via a pair of fasteners. Proximal first opening 222 may be circular, as shown here, or oblong. Distal first opening 224 also may be circular, or may be oblong as shown here. In particular, the distal first opening may be oblong in a direction transverse to the long axis of the bone plate. The distal first opening thus may allow the bone plate to be coupled to the nail over a range of angles permitted by a fastener disposed in distal first opening 224 when the bone plate is pivoted about an axis defined by another fastener disposed in proximal first opening 222. The bone plate may extend proximally (generally toward the trailing end of the nail) any suitable distance when the bone plate is coupled to the nail. For example, the bone plate may extend past the proximal first opening by a distance substantially less a longitudinal dimension of the nail from its most rearward transverse aperture to the trailing end of the nail, such that the nail extends closer to the end of the bone than the bone plate.

Second plate portion 214 may define second openings 226, 228 for placement of fasteners obliquely into bone. The second openings may be oblong in a direction generally parallel to the long axis of the bone plate, as shown here. Furthermore, each of the second openings may have a proximal wall (closest to the first plate portion) defining an oblique placement axis 230 for each of the oblique fasteners (see FIG. 8). Each oblique placement axis may be about 110-140 degrees, or about 125 degrees, among others. The oblique placement axes may be parallel to each other or may be nonparallel. In some embodiments, the second plate portion may have only one second opening or may have three or more second openings.

Bone plate 210 may have projections, such as ridges 232, formed by an inner surface 234 of the bone plate. The ridges may be disposed around each opening, such that the bone plate is thicker at positions near the openings and thinner elsewhere. Ridges 232 may function to hold most of inner surface 234 above the exterior bone surface and/or to reinforce the bone plate at the positions of the openings.

Figure 9:
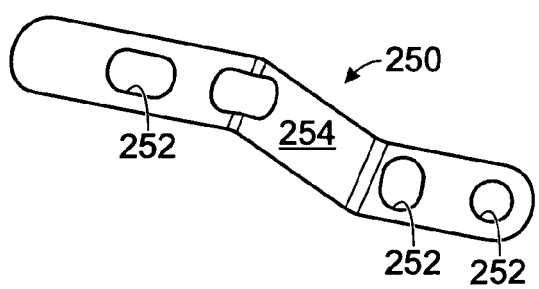
FIG. 9 is a top view of another exemplary bone plate that may be employed by the systems of the present disclosure.

FIG. 9 shows a top view of another exemplary bone plate 250 that may be included in fixation devices of the systems of the present disclosure. Bone plate 250 may include a countersink 252 formed in an outer surface 254 of the bone plate around one or more of the plate openings.

Figure 10:
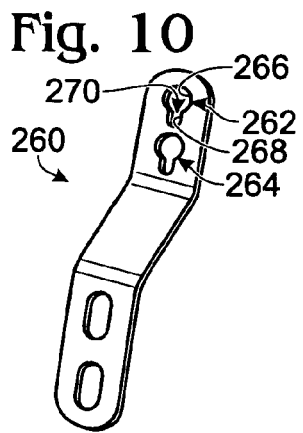
FIG. 10 is a top view of yet another exemplary bone plate that may be employed by the systems of the present disclosure.

FIG. 10 shows yet another exemplary bone plate 260 that may be included in the systems of the present disclosure. Bone plate 260 may have any aspects of the bone plates described elsewhere in the present disclosure, for example, bone plate 260 may be similar in construction to bone plate 210 (FIGS. 7 and 8), among others. However, bone plate 260 may be configured to be coupled to fasteners that are already disposed in bone. In particular, the bone plate may include one or more two-part first openings 262, 264 for alignment with one or more transverse apertures of a nail. Each two-part opening may include a receiver region 266 adjoining a retainer region 268. The receiver region may have a larger width than the retainer region, to permit a head region of a fastener to be received by the receiver region, from the inner surface of the bone plate, and then retained by the retainer region. Each region may be circular, that is, corresponding to an arc of a circle, or may be noncircular. In some embodiments, the regions may form a narrowed area 270 where the regions meet one another. The narrowed region may have a width that is less than the maximum width of the retainer region. Each two-part opening may be oriented longitudinally, as shown here, or transversely with respect to the long axis of the bone plate.

Figure 11:
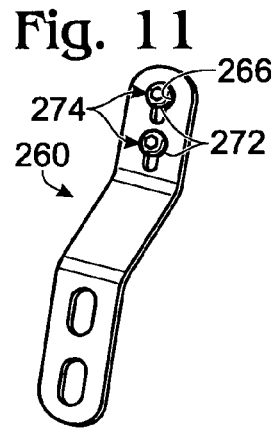
FIG. 11 is a top view of the bone plate of FIG. 10 after the bone plate has received a head region of each of a pair of fasteners already disposed in bone, with the bone plate in an unsecured position, in accordance with aspects of the present disclosure.

FIG. 11 shows bone plate 260 after the bone plate has received a head region 272 of each of a pair of transverse fasteners 274 that already are disposed in bone (and, optionally, already extending into and/or through transverse apertures of a nail disposed in bone). Each head region is disposed in a respective receiver region 266 of a two-part first opening. Here, the bone plate is in an unsecured position because the bone plate can be separated from the fasteners by lifting the bone plate off of bone in a direction parallel to the long axes of the transverse fasteners.

In some embodiments, the bone plate may have only one two-part first opening, which may be disposed more proximally or more distally in the first plate portion. Accordingly, the bone plate may receive transverse fasteners in a pair of first openings from opposing directions, that is, respectively from below the inner surface and from above the outer surface of the bone plate.

Figure 12:
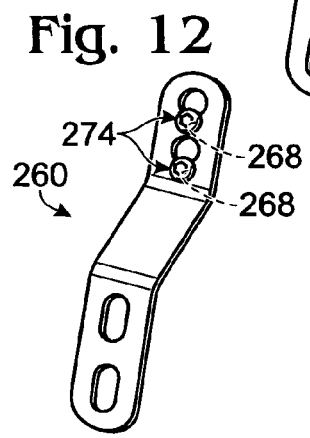
FIG. 12 is a top view of the bone plate and pair of fasteners of FIG. 11 after the bone plate has been moved to a retained position, in accordance with aspects of present disclosure.

FIG. 12 shows bone plate 260 after transverse fasteners 274 have been shifted to respective retainer regions 268 by longitudinal movement of the bone plate. The bone plate then may be restricted from reverse longitudinal movement back to the position of FIG. 11, by turning the transverse fasteners into engagement with the retainer region of each opening.

III. FASTENERS

A fastener, as used herein, generally comprises any device for attaching a nail to bone, a buttress member to bone, a nail to a buttress member, or bone fragments/bones to each other. Each fastener may be a discrete device that is placed into bone before or after the nail is placed into bone and/or the buttress member is placed onto bone. The fastener may lock to the nail, buttress member, and/or bone; or may engage the nail, buttress member, and/or bone in a nonlocking fashion. Exemplary fasteners may include screws, pins, wires, rivets, and/or the like.

The fastener may be a threaded fastener, that is, a fastener with at least one external thread for locking the fastener to bone, the nail, and/or the buttress member. The threaded fastener may include a shank distally and a head proximally. The shank may be linear and may include at least one threaded region. The head may be any proximal structure that has a greater diameter than the shank.

The shank may include a thread extending along any suitable portion (or all) of the length of the shank. The thread may have a uniform pitch or the pitch may change, such as decreasing toward the head. In some embodiments, the shank may include at least two interspersed threads following distinct helical or helix-like paths (to provide a multi-threaded shank). The thread may be relatively deep, such as the thread on a cancellous bone screw, or may be relatively shallow, such as the thread on a cortical bone screw.

The head of the threaded fastener may have any suitable structure. Generally, the head defines a driver-engagement structure adjacent a proximal end of the fastener for driving the fastener into bone with a driver. Exemplary driver-engagement structures may include a socket, a slot(s), external facets, and/or the like. The head may include or lack an external thread. The head may be structured to be self-drilling and/or self-tapping. If the head lacks an external thread, the head may have a bearing surface for engagement of bone and/or a buttress member.

The threaded fastener may have any other suitable features. In some embodiments, the threaded fastener may define a longitudinal passage, such that the fastener is cannulated (e.g., for placement of the fastener over a pre-installed guide wire or guide pin).

Figure 13:
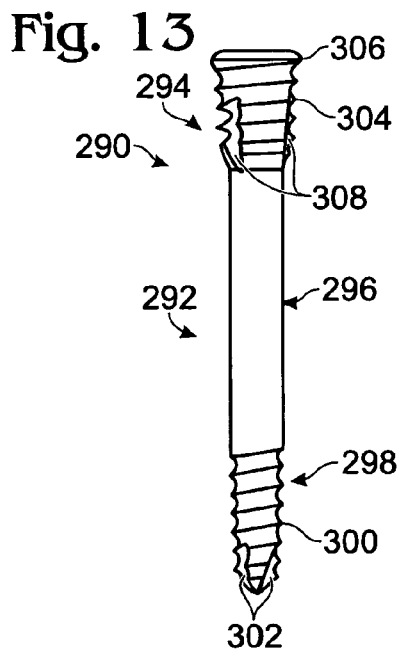
FIG. 13 is a side view of an exemplary fastener that may be employed by the systems of the present disclosure.

FIG. 13 shows an exemplary threaded fastener 290 that may be included in the systems of the present disclosure. Fastener 290 may be described as a bone screw, with a shank 292 extending from a head 294.

Shank 292 may include a nonthreaded proximal section 296 adjacent head 294 and a threaded distal section 298 joined to proximal section 296. The proximal section of shank 292 may have a diameter that is about the same as, less than, or greater than the major diameter of the threaded distal section 298. In addition, the proximal section of shank 292 may have a uniform diameter, as shown here, or the diameter may be nonuniform along the length of the proximal section. Threaded distal section 298 may include an external thread 300 that forms a threaded tip of the fastener, and may taper toward the leading end of the fastener, as shown here, or may have a uniform major diameter. In addition, the threaded distal section may include one or more flutes 302 that impart a drilling and/or tapping capability to the shank of the fastener.

Head 294 may include an external thread 304 extending to a proximal flange 306. The external thread may have a greater diameter than the diameter of nonthreaded proximal section 296 and/or greater than the major diameter of the threaded distal section 298. The external thread may decrease in major diameter (and/or minor diameter) toward the shank, shown here, or may have a uniform major diameter (and/or minor diameter). The head also may include one or more flutes 308 that impart a drilling and/or tapping capability to the head of the fastener. In some embodiments, proximal flange 306 may provide a stop that restricts excessive advancement of the fastener through the opening of a buttress member and/or into bone.

External thread 300 of shank 292 and external thread 304 of head 294 may have any suitable pitch relationship. For example, threads 300 and 304 may have about the same pitch or may have different pitches (e.g., with thread 300 having a pitch that is greater than that of thread 304), to provide compression of bone fragments and/or of a buttress member with bone.

IV. COMPOSITION OF SYSTEM COMPONENTS

Each system component may have any suitable composition. For example, the system component, and particularly a nail, buttress member, and/or fastener constituting a fixation device of the system, may be formed of a biocompatible and/or bioresorbable material. Exemplary biocompatible materials that may be suitable include a biocompatible metal (e.g., stainless steel, titanium, a titanium alloy, and/or cobalt-chrome, among others), plastic, ceramic, composite, and/or the like. Exemplary bioresorbable materials that may be suitable include bioresorbable polyesters, such as polylactide, polyglycolide, or polylactide/polyglycolide copolymers, among others.

The nail, buttress member, and fasteners of a fixation device may be formed of the same class or different classes of materials. For example, the nail, buttress member, and fasteners each may be formed of metal, such as all formed of the same metal/metal alloy (e.g., stainless steel, titanium, or titanium alloy) or at least two may be formed of different metals/metal alloys. Alternatively, at least two components of the fixation device may be formed of different classes of materials, such as a nail formed of metal and a buttress member formed of plastic, or vice versa, among others.

V. METHODS OF FIXING BONES USING A NAIL COUPLED TO A BUTTRESS MEMBER

The present disclosure provides methods of fixing bones, particularly a femur fractured proximally (or distally). Exemplary method steps that may be performed are presented below. Each of the method steps may be performed in any suitable order, in any suitable combination, and any suitable number of times.

A bone may be selected for fixation. The bone may be a long bone and may be selected for any suitable reason, such as the presence of one or more discontinuities (e.g., fractures or cuts in the bone), a structural weakness, a nonunion, an undesired length, an undesired shape, and/or the like. In some embodiments, the selected bone may include a cut through the bone introduced a short time before a fixation device is installed to fix the bone (e.g., during the same surgical procedure).

The bone selected may have any suitable number of discontinuities disposed in any suitable region(s) of the bone. For example, the bone may have one or more discontinuities disposed proximally, centrally, and/or distally. Accordingly, each discontinuity may be disposed in a metaphyseal (end) or diaphyseal (shaft) region of a bone. Furthermore, each discontinuity may be transverse and/or longitudinal. In some embodiments, the bone selected may include at least one fracture of the bone's shaft and at least one other fracture near the end of the bone.

Fragments of the selected bone may be repositioned in accordance with the anatomy of the bone, that is, the fracture(s) may be reduced by aligning and/or re-orienting the fragments.

The selected bone may be prepared for receiving a nail. A proximal or distal end region of the bone may be accessed by creating an incision over the end region. For example, to access the proximal end of a femur, a lateral incision may be introduced that extends over the proximal end of the greater trochanter. In any event, the medullary canal of the selected bone then may be opened by creating a hole, such as with an awl, through the end region of the bone and into the medullary canal. The medullary canal then may be enlarged by reaming the canal one or more times. In some embodiments, the medullary canal may be reamed relatively more deeply (a greater distance) with a smaller diameter reamer, and also may be reamed relatively less deeply (a shorter distance) with a larger diameter reamer. The smaller diameter reamer may prepare the canal for receiving a distal tip portion of a nail and/or for seating a finned region of the nail, and the larger diameter reamer may prepare the canal for slidably receiving the finned region and/or a proximal body portion of the nail.

Figure 14:
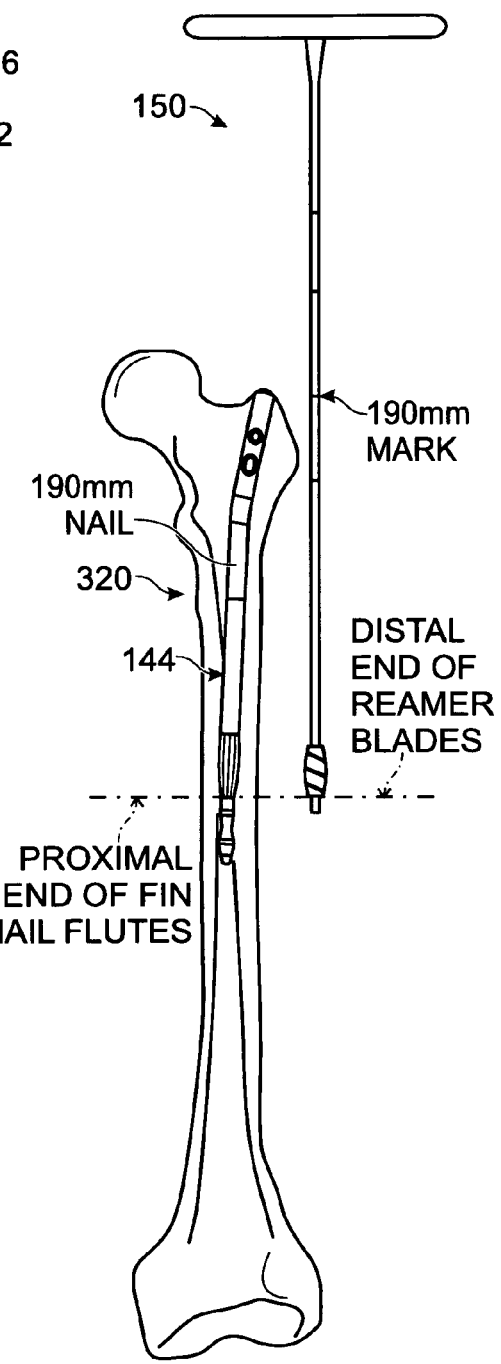
FIG. 14 is a view of a fractured left femur with a fin nail of FIG. 3 disposed in the intramedullary canal of the femur and with the reamer of FIG. 3 disposed adjacent the bone and positioned to indicate how far the reamer should be advanced into the medullary canal prior to placement of the fin nail, in accordance with aspects of the present disclosure.

FIG. 14 shows an exemplary selected bone, a fractured left femur 320, with fin nail 144 of FIG. 3 disposed in the intramedullary canal of the femur. Here, reamer 150 of FIG. 3, which corresponds to a reamer of relatively larger diameter, is disposed adjacent the bone and positioned longitudinally to indicate how far reamer 150 was advanced into the medullary canal prior to placement of the fin nail. A nail may be placed longitudinally into the medullary canal of the selected bone.

The nail may have any of the features shown and/or described elsewhere in the present disclosure. For example, the nail may be a fin nail or a nail without fins. The nail may be selected from a set of nails of different length and/or diameter, based, for example, on a measurement of the medullary canal and/or selected bone. In some embodiments, the nail may be selected based on observation of reference marks disposed along a reamer. The nail may be placed into the medullary canal such that a trailing end of the nail is approximately flush with, or recessed with respect to, an end region of the bone.

One or more fasteners may be placed through bone and into and/or through one or more transverse holes of the nail. The one or more fasteners may be placed through transverse holes disposed in a trailing region and/or a leading region of the nail. The fasteners may have one or more threaded regions that engage bone on one side (the near side or far side) or on opposing sides of the nail. Holes may be drilled for the fasteners prior to fastener placement, or each fastener may be self-drilling and thus capable of forming its own hole during fastener placement.

FIGS. 15 and 16 show an exemplary handle 330 and targeting guide 332 that may be used, respectively, for placing a nail (e.g., fin nail 144) into bone and for drilling holes and/or placing fasteners through transverse holes 334, 336 of nail 144. Handle 330 may threadably coupled to nail 190 and may provide an attachment site for targeting guide 332.

A buttress member, such as a bone plate, may be attached to the selected bone. The buttress member may be attached as described elsewhere in the present disclosure. The buttress member may be positioned generally longitudinally on an exterior surface region of the bone, with one or more first openings of the buttress member aligned with one or more transverse apertures of the nail, and with one or more second openings of the buttress member disposed more centrally on the bone and closer to the leading end of the rod. In some embodiments, the buttress member may be selected from a set of at least two buttress members (e.g., buttress members with mirror-image symmetry) that respectively place the second openings generally on opposing sides of the nail, such as respective buttress members that place the second openings anteriorly or posteriorly (or medially or laterally) to the nail. Furthermore, the same buttress member may be used on opposing sides of the body to position oblique fasteners on opposing sides of respective left and right nails. For example, the same buttress member that may be used to position an oblique fastener(s) anteriorly to a nail on a left femur may be used instead on a right femur to position an oblique fastener(s) posterior to a nail. Accordingly, only two plates may be necessary for both sides of the body and selective placement on opposing sides of the nail.

In any event, the buttress member may be positioned on the bone, and in alignment with the nail, before or after one or more of the fasteners have been placed into/through the nail. For example, the buttress member may be received on one or more pre-installed fasteners (see FIGS. 10-12). In some embodiments, the buttress member may be received on only one pre-installed fastener and then another fastener may be placed first through another first opening of the buttress member, into bone, and then into/through a transverse aperture of the nail.

FIG. 17 shows an exemplary configuration produced during installation of fixation device 44 of FIG. 1 into a fractured femur. A more proximal transverse fastener 70 extends through bone plate 64 and nail 62.

Figure 18:
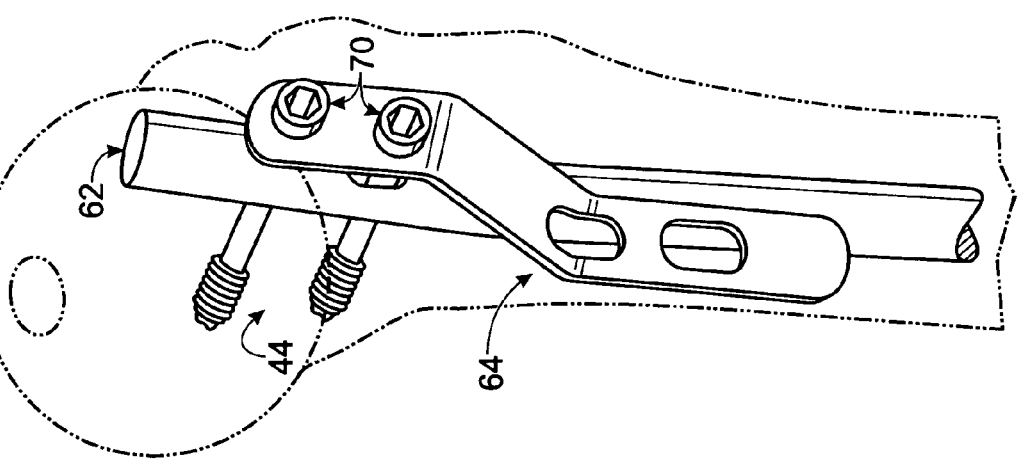
FIG. 18 is another view of the fractured femur of FIG. 17 taken at a later intermediate stage of an exemplary method of fixing bone.

FIG. 18 shows another exemplary configuration produced during installation of fixation device 44 of FIG. 1. Here, both proximal and distal transverse fasteners 70 extend through bone plate 64, the lateral cortex, and nail 62 to attach the bone plate to bone and to couple the bone plate to the nail. The proximal and/or distal transverse fasteners may or may not span a pertrochanteric fracture and thus may or may not extend into the medial cortex, the neck, and/or head of the femur.

One or more oblique fasteners may be placed obliquely through second openings of the bone plate and in a direction generally toward the trailing end of the nail. The oblique fasteners may extend to one side (or to both sides) of the nail, such as anterior to the nail and/or posterior to the nail. Alternatively, or in addition, one or more of the oblique fasteners may extend through the nail. In some embodiments, only one of the second openings of the bone plate may be selected for placement of an oblique fastener. The second opening may be selected based, for example, on the size/geometry of the bone in the particular individual into which the fixation device is being installed. In some embodiments, at least two second openings of the bone plate may be selected for placement of an oblique fastener. The oblique fastener(s) may be placed into a pre-formed hole or may form it/their own hole(s) during placement. In some embodiments, a guide pin may be placed into the pre-formed hole (or may be placed to guide hole formation) for guiding placement of an oblique fastener. The guide pin may be used in place of fluoroscopy with C-arm intensification. In exemplary embodiments, for the purposes of illustration only, the oblique fastener may be a 6.3 mm (diameter) fastener. In any event, the oblique fastener(s) may be placed through a fracture, in a direction generally perpendicular to a plane defined by the fracture. The oblique fastener may thread into bone on the far side, the near side, or both far and near sides of the fracture. The oblique fastener also or alternatively may lock to the bone plate. In some embodiments, an additional oblique fastener may be placed through the fracture without extending through the plate. For example, if an oblique fastener is placed through the bone plate anteriorly to the nail, an additional oblique fastener may be placed posteriorly to the nail.

Placement of the oblique fastener(s) may include compression of the bone. For example, the oblique fastener(s) may be a lag screw with only a distal threaded region or may be a fastener with spaced threaded regions of different pitch.

Figure 19:
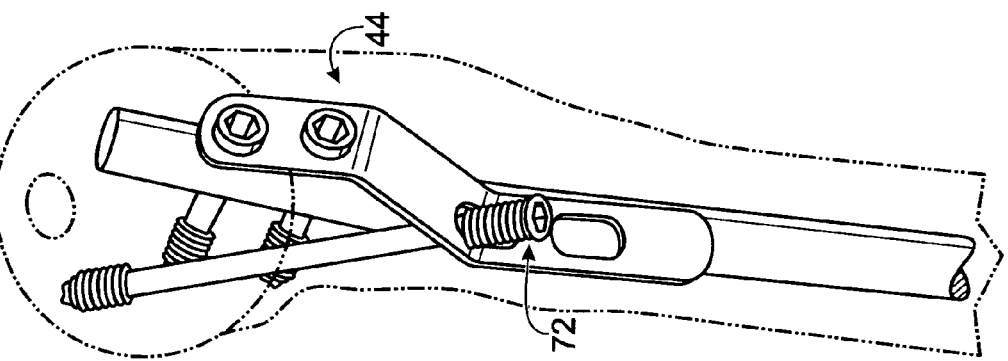
FIG. 19 is yet another view of the fractured femur of FIG. 17 taken at an even later intermediate stage (or after completion) of an exemplary method of fixing bone.

FIG. 19 shows yet another exemplary configuration produced during installation of fixation device 44 of FIG. 1. Here, a more proximal oblique fastener 72 has been placed through a more proximal second opening of the plate such that fastener 72 spans a pertrochanteric fracture and extends anteriorly to the nail and into the head of the femur. At this stage, a practitioner may elect to install no other oblique fasteners and thus installation of fixation device 44 may be complete.

Figure 20:
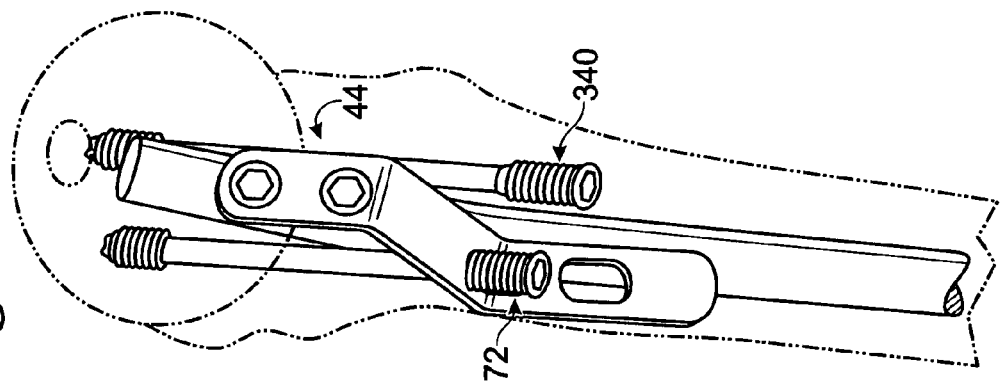
FIG. 20 is still another view of the fractured femur of FIG. 17 taken at a still later intermediate stage (or after completion) of an exemplary method of fixing bone.

FIG. 20 shows still another exemplary configuration produced during installation of fixation device 44 of FIG. 1. Here, another fastener 340 has been placed obliquely into the head of the femur from an opposing side of the nail relative to oblique fastener 72. Fastener 340 does not extend through an opening of the bone plate. At this stage, a practitioner may elect to install no other oblique fasteners and thus installation of fixation device 44 may be complete.

Figure 22:
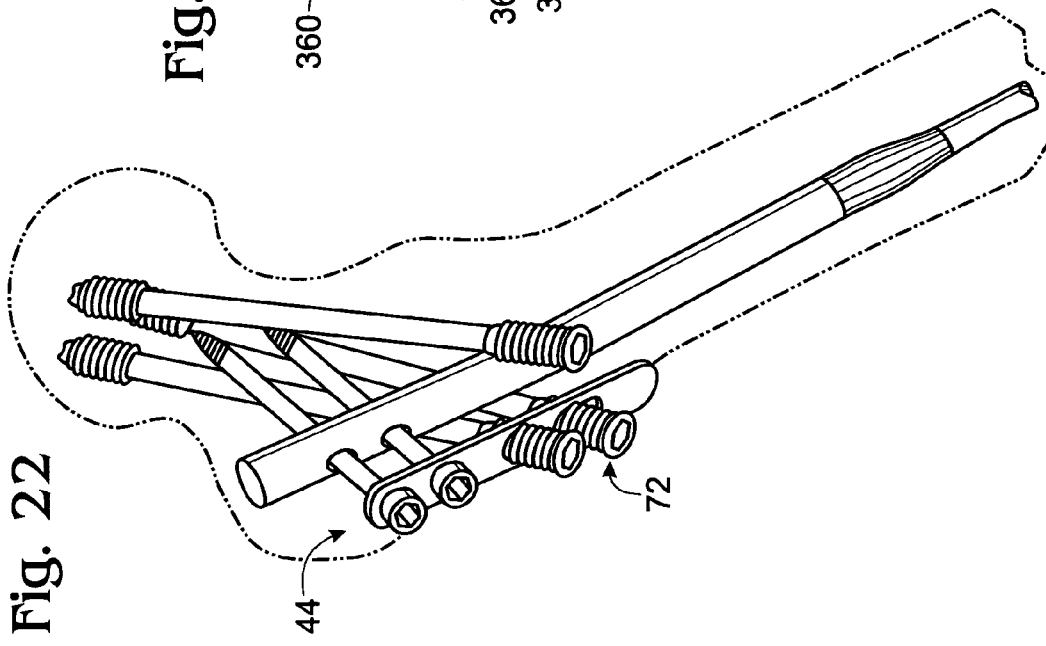
FIGS. 21 and 22 are other views of the fractured femur of FIG. 17 taken after an exemplary completion of an exemplary method of fixing bone.
Figure 21:
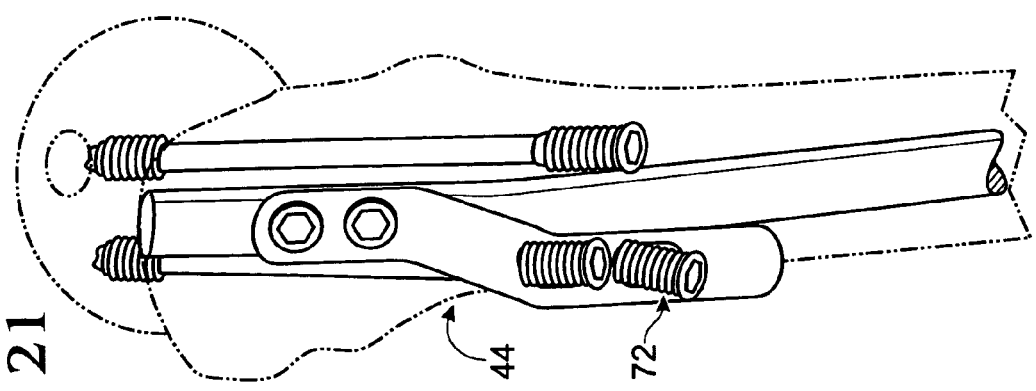

FIGS. 21 and 22 show distinct views of still yet another exemplary configuration produced during installation of fixation device 44 of FIG. 1. Here, another oblique fastener 72 has been placed through a more distal second opening of the bone plate and into the head of the femur. Alternatively, a practitioner may elect to omit placement of the more proximal oblique fastener and only use the more distal second opening of the bone plate. Furthermore, if both second openings of the bone plate are being used, the oblique fasteners may be placed into bone in any suitable order.

Further aspects of nail installation are described in U.S. Pat. No. 7,066,943 and in U.S. Provisional Patent Application Ser. No. 60/957,145, which are incorporated herein by reference.

VI. SYSTEMS/KITS FOR FIXING BONES USING A NAIL COUPLED TO A BUTTRESS MEMBER

The present disclosure provides systems and/or kits for bone fixation. Each system/kit may include at least one nail, at least one buttress member, and/or a plurality of fasteners for interlocking the nail and the bone plate to each other and to bone. In some embodiments, the system/kit may include two or more nails of different size (e.g., different lengths and/or diameters) and/or type (e.g., finned and non-finned) for use with the same buttress member. In some embodiments, the system/kit may include two or more buttress members of different size, shape, and/or handedness (e.g., a pair of plates with substantial mirror-image symmetry) for alternative use with the same nail or for use with each of two or more nails of different size. The system/kit also or alternatively may include two or more fasteners of different length, diameter, thread configuration, and/or the like. The system/kit further may include at least one reamer, a targeting guide to guide hole formation in bone and/or fastener placement (such as defining an axis that extends through a transverse hole of the nail), an attachable/removable handle for manipulating the nail, a drill, a driver for the fasteners, a removal tool for the nail, and/or instructions for use, among others. One or more (or all) of the system/kit components may be provided in a substantially sterile condition, such as packaged in an enclosure, which, optionally, may be sealed hermetically. Alternatively, or in addition, one or more (or all) of the system/kit components may be provided in a non-sterile condition.

VII. EXAMPLES

The following examples describe selected aspects and embodiments of the present disclosure, particularly an exemplary bone plate; exemplary fixation devices including a nail, a buttress member, and fasteners; and exemplary methods of fixing bone by installation of fixation devices including a nail and a buttress member that couples to the nail. These examples and the various features and aspects thereof are included for illustration and are not intended to define or limit the entire scope of the present disclosure.

Example 1

Exemplary Bone Plate

Figure 23:
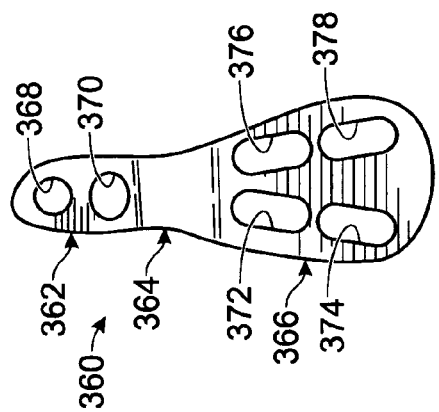
FIG. 23 is a plan view of an exemplary bone plate that allows placement of oblique fasteners through the bone plate on both opposing (anterior and posterior) sides of a nail, in accordance with aspects of the present disclosure.

This example describes an exemplary bone plate 360 that permits placement of oblique fasteners on either or both opposing sides of a nail; see FIG. 23.

Bone plate 360 may include a first plate portion 362, a bridge portion 364, and a second plate portion 366. The bone plate may have any of the features described elsewhere in the present disclosure. For example, the first plate portion may define first openings 368, 370 for receiving transverse fasteners that couple the bone plate to a nail, as described elsewhere in the present disclosure. In addition, the first plate portion may be elevated with respect to the second plate portion, or vice versa. However, the second plate portion may define second openings 372-378 that are offset bilaterally from first openings 368, 370. In particular, the second openings may be offset laterally to opposing sides of a central z-plane extending orthogonally through first plate portion 362. Accordingly, bone plate 360 may allow a practitioner to place oblique fasteners through the bone plate and to both opposing sides (e.g., posterior and/or anterior) of the nail. The same bone plate 360 may be used on both sides of the body or the bone plate may be manufactured as left-side and right-side versions for use on corresponding sides of the body.

Example 2

Exemplary Fixation Device with an Interlocked Nail and Plate

This example describes an exemplary fixation device 400 including an intramedullary nail 402 and a plate 404 interlocked to each and to bone by a pair of fasteners 406, 408 disposed in a femur 410; see FIGS. 24 and 25. Femur 410 may have an oblique fracture 411 (see FIG. 25).

Plate 404 may have any of the features described elsewhere in the present disclosure. For example, plate 404 may have at least one proximal elongate opening 412 (i.e., a proximal slot) and at least one distal elongate opening 414 (i.e., a distal slot).

The slots may extend longitudinally with respect to the plate, as shown here. The proximal slot (and/or the distal slot) may form a receiver region 416 and a retainer region 418. The receiver region may be wide enough for the head of proximal fastener 406 to pass through the slot from the inner surface of the plate. The retainer region may be narrow enough to restrict passage of the fastener head through the slot.

Distal fastener 408 may be placed posteriorly (or anteriorly) to nail 402. The femur may be further stabilized by another threaded fastener 420 placed anteriorly (or posteriorly) to nail 402, but generally without intersecting plate 404.

Example 3

Exemplary Fixation Device with an Adjustable Buttress Member

This example describes an exemplary fixation device 450 including an intramedullary nail 452 and an adjustable buttress member 454 interlocked with each other and with bone by a pair of fasteners 456, 458; see FIGS. 26-29.

Figure 27:
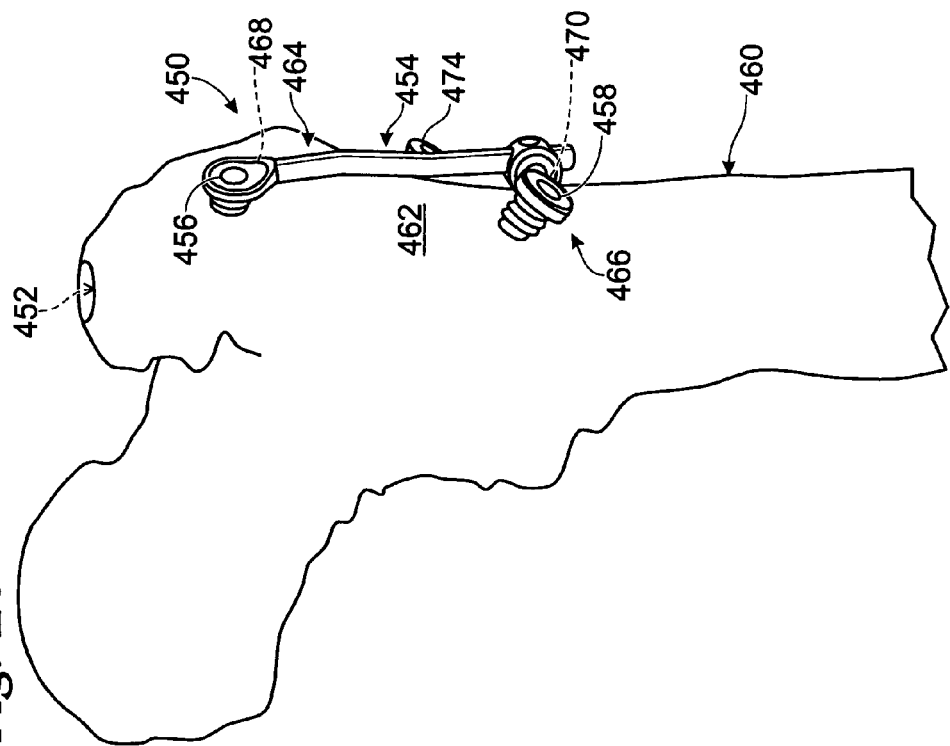
FIG. 27 is a view of the femur and fixation device of FIG. 26, taken as in FIG. 26, but with the femur hiding all portions of the fixation device that are inside bone.
Figure 26:
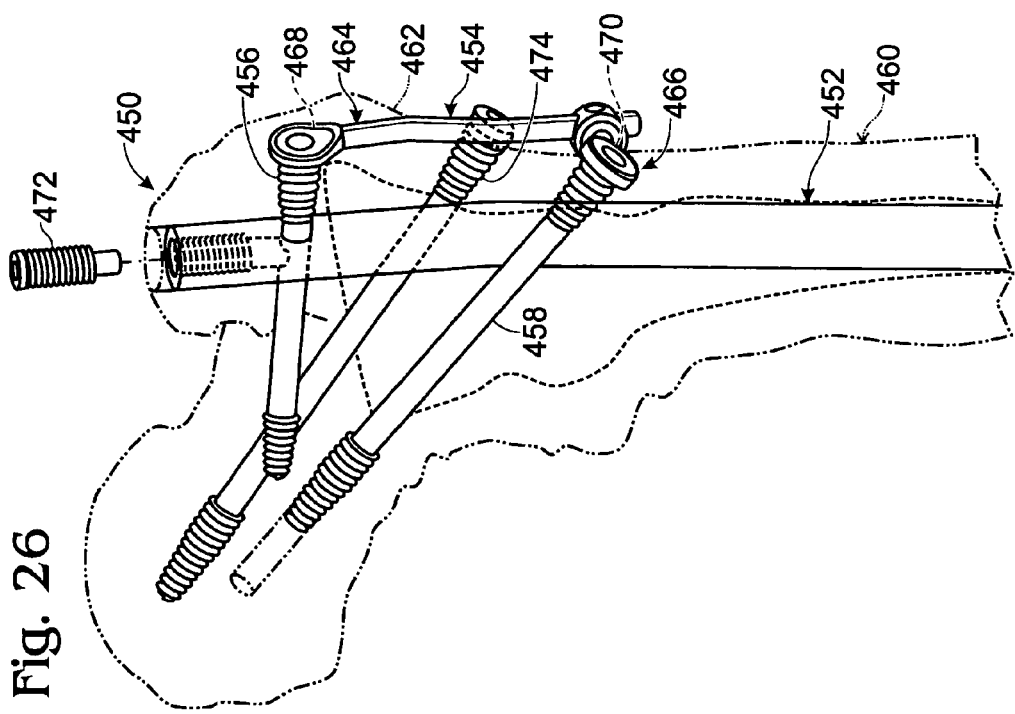
FIG. 26 is a view of a fractured femur being fixed proximally with an exemplary fixation device including an intramedullary nail and an adjustable buttress member, with the nail and the buttress member separated by bone and interlocked by a threaded fastener disposed in the femur, in accordance with aspects of the present disclosure.

FIGS. 26 and 27 show fixation device 450 installed in and on a fractured femur 460. Nail 452 may be disposed in a proximal region of the femur's medullary canal. Buttress member 454 may be disposed on an exterior surface region 462 of the femur. The exterior surface region may be lateral of the nail such that the buttress member is laterally offset from and extends generally parallel to the nail.

Buttress member 454 may include at least a pair of discrete anchor portions for receiving fasteners such as threaded fasteners 456, 458. For example, buttress member 454 may have a first anchor portion 464 connected to at least one discrete second anchor portion 466. Each anchor portion may define at least one opening for receiving a fastener. Here, first anchor portion 464 defines a proximal opening 468 and second anchor portion 466 defines a distal opening 470. Proximal and distal openings 468, 470 may receive respective fasteners 456, 458, which interlock nail 452 with buttress member 454 and with bone (i.e., fragments of femur 460). Proximal fastener 456 may be further stabilized by a longitudinal fastener 472 placed longitudinally into nail 452 and into threaded engagement with the nail from a trailing terminus thereof. The longitudinal fastener may be advanced until its leading end bears against a side of proximal fastener 456, which may restrict turning and longitudinal movement of the proximal fastener relative to the nail.

Femur 460 may be further stabilized by at least one other fastener, such as distal, anterior fastener 474. Fastener 474 may or may not extend through an anchor portion of buttress member 454. In some embodiments, the buttress member may have one or more second anchor portions that define distal openings on opposing sides of the buttress member, to permit the buttress member to be attached to bone with fasteners extending through both anterior and posterior distal openings. In some embodiments, the second anchor portion of the buttress member may extend only anteriorly from the first anchor portion, rather than posteriorly as shown here.

Figure 28:
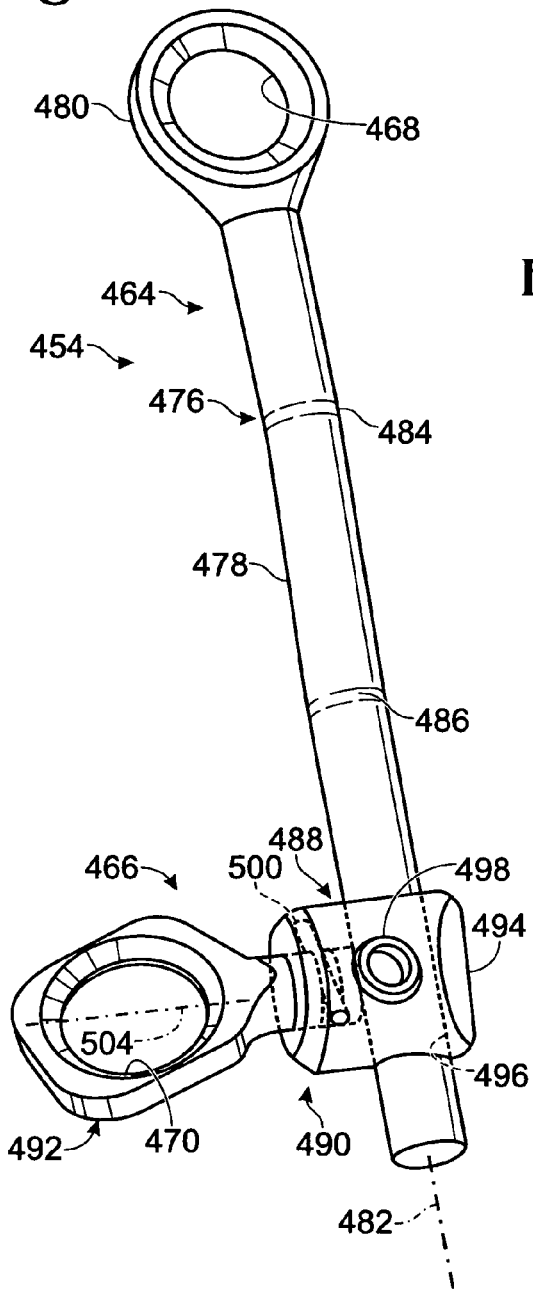
FIG. 28 is a plan view of the adjustable buttress member of FIG. 26 taken by itself.
Figure 29:
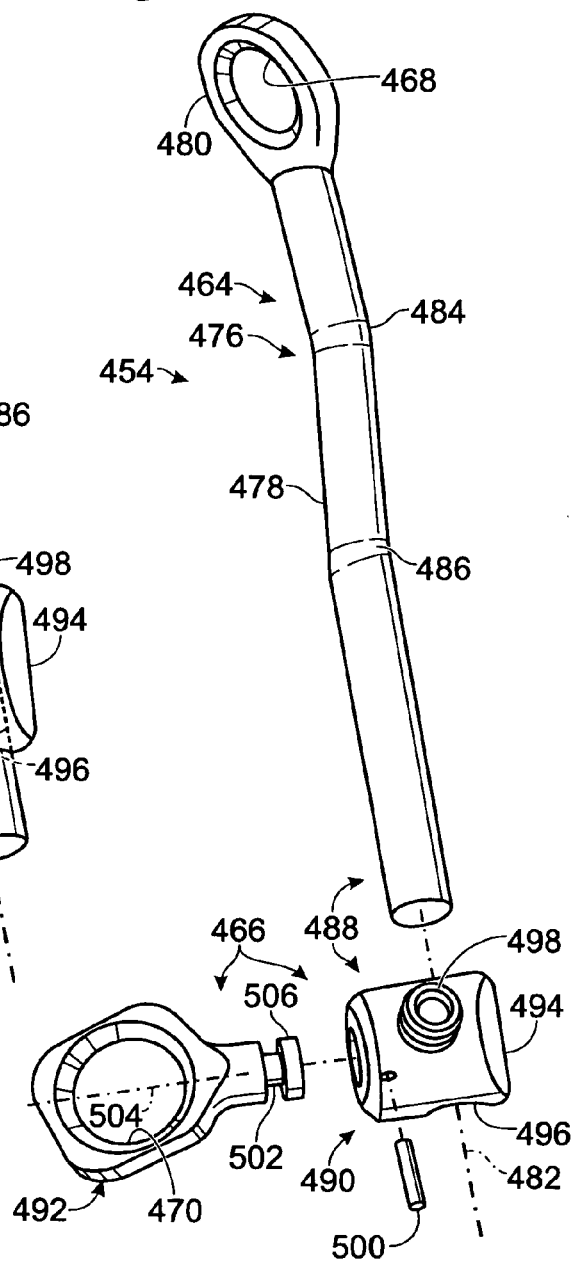
FIG. 29 is an exploded view of the adjustable buttress member of FIG. 28.

FIGS. 28 and 29 show buttress member 454 in isolation and in respective assembled and exploded configurations. First anchor portion 464 may form an elongate body 476 of the buttress member. Body 476 may include a rod region 478 and a widened head region 480 extending proximally from the rod region. The rod region may define a long axis 482 and may be generally linear, as shown here. However, the rod region may be bent at one or more bent sections 484, 486, to permit the rod region to more closely follow a surface contour of bone and thus maintain a lower profile above the bone.

First anchor portion 464 and second anchor portion 466 may be connected by a movable joint 488. The movable joint may have an adjustable configuration and a locked configuration (also termed a fixed configuration). In the adjustable configuration, second anchor portion 466 can slide along rod region 478 (i.e., parallel to long axis 482), can slide at least partway around the rod region 478 (i.e., by pivotal motion about long axis 482, or both. In the locked configuration, the second anchor portion may be restricted from sliding along and/or about long axis 478.

Second anchor portion 466, which also may be termed a sidearm assembly, may include a carriage assembly 490 connected to a loop element 492. Carriage assembly 490 may include a body 494 defining a cavity 496 that is sized and shaped to receive a segment of rod region 478, such that the carriage body can slide along the rod region (and vice versa). The carriage assembly also may include one or more fasteners coupled to carriage body 494. For example, a lock screw 498 may be threadably engaged with carriage body 494 and may be turned to adjust engagement of the carriage assembly with the rod region, thereby permitting or restricting relative movement of the carriage assembly and the rod region. Alternatively, or in addition, the carriage assembly may include a retainer, such as a pin 500, that resists separation of loop element 492 from carriage assembly 490. Pin 500 may, for example, be press-fit into a channel defined by carriage body 494 to partially occupy an annular channel 502 defined by loop element 492. The loop element thus may be pivoted about a transverse axis 504 defined by rod region 478 (and/or carriage assembly 490). However, separation of the loop element from the carriage assembly may be restricted by an annular flange 506 that forms a wall of annular channel 502 (see FIG. 29). Pivotal motion of loop element 492 may be permitted whether or not carriage assembly 490 is locked to rod region 478.

Loop element 492 may define one or more openings for receiving fasteners that attach the buttress member to bone. For example, here, loop element 486 defines a circular opening (distal opening 470) via a closed loop. In other examples, the loop element may define an elongate opening (i.e., a slot) and/or may form an open loop.

An adjustable and/or rod-based buttress member may have substantial advantages over non-adjustable and/or non-rod-based buttress members. For example, an adjustable buttress member may permit a single device to be used with different sizes of femurs, different neck angles of different femurs, and distinct fracture configurations. Moreover, the single device may permit the distal opening to extend anteriorly or posteriorly from the rod region (by pivoting the second anchor portion to an opposing side of the rod region), for corresponding anterior or posterior attachment of the buttress member to bone. In addition, another second anchor portion may be coupled to rod region 478, to permit both anterior and posterior attachment of the buttress member to bone. With two second anchor portions, each second anchor portion may be adjusted independently. Also, in some embodiments, the second anchor portion may have opposing loop elements extending from the same carriage assembly to permit anterior and posterior attachment of the buttress member to bone. Furthermore, a rod-based buttress member may be substantially stronger than a plate-based buttress member and thus may provide better stabilization of a fractured femur.

Example 4

Selected Embodiments

This example describes selected embodiments of the present disclosure, presented as a series of indexed paragraphs.

1. A device for bone fixation, comprising:
an intramedullary nail for placement longitudinally into a medullary canal of a bone and including a leading section and a trailing section, the intramedullary nail defining a long axis and also defining one or more transverse apertures in the trailing section;
a plurality of fasteners including one or more first fasteners and one or more second fasteners for placement into the bone; and
a bone plate for placement adjacent an exterior surface region of the bone, the bone plate including longitudinally arranged first and second plate portions, the first plate portion defining one or more first openings for alignment with the one or more transverse apertures such that the one or more first fasteners, when disposed in the bone, can extend at least from a first opening to a transverse aperture to couple the intramedullary nail to the bone plate, the second plate portion defining at least one second opening for receiving at least one second fastener at an angle oblique to the long axis, when the intramedullary nail is coupled to the bone plate via the first plate portion, such that the at least one second fastener extends adjacent and past the intramedullary nail in a direction generally toward a trailing end thereof for engagement of a peripheral bone fragment.

2. The device of paragraph 1, wherein the leading section of the intramedullary nail includes at least one fin.

3. The device of paragraph 2, wherein the leading section of the intramedullary nail includes an elongate tip region and a finned region disposed rearward of the elongate tip region, wherein the elongate tip region is narrower than the finned region, wherein the finned region includes a plurality of longitudinal fins, and wherein the intramedullary nail rearward of the finned region is narrower than the finned region.

4. The device of paragraph 1, wherein the trailing section of the intramedullary nail defines at least two transverse apertures.

5. The device of paragraph 4, wherein each of the at least two transverse apertures is a through-hole.

6. The device of paragraph 5, wherein one or more of the at least two transverse apertures is elongate in a direction generally parallel to the long axis of the rod.

7. The device of paragraph 1, wherein the intramedullary nail has a leading end and a trailing end, wherein the one or more transverse apertures are disposed closer to the trailing end, and wherein the intramedullary nail also defines one or more other transverse apertures closer to the leading end.

8. The device of paragraph 1, wherein the plurality of fasteners includes a bone screw having a leading threaded section and a trailing threaded section that are spaced from each other.

9. The device of paragraph 8, wherein the leading threaded section has a smaller maximum diameter than the trailing threaded section.

10. The device of paragraph 8, wherein the leading threaded section has a larger pitch than the trailing threaded section to provide compression when the bone screw is installed in bone.

11. The device of paragraph 8, wherein the leading threaded section and a trailing threaded section are separated by a nonthreaded shank portion of the bone screw.

12. The device of paragraph 8, wherein the bone screw has a head, and wherein the trailing threaded section forms a least part of the head.

13. The device of paragraph 1, wherein the first and second plate portions are offset laterally from one another.

14. The device of paragraph 1, wherein each of the first and second plate portions defines two or more openings.

15. The device of paragraph 1, wherein the first plate portion is elevated relative to the second plate portion.

16. The device of paragraph 1, wherein the bone plate is configured to be placed into engagement with at least one of the one or more first fasteners after the at least one first fastener has been placed into the bone and into a transverse aperture of the intramedullary nail.

17. The device of paragraph 16, wherein at least one of the one or more first openings of the first plate portion has a receiver region and a retainer region, wherein the receiver region is relatively larger in width to receive a first fastener from a trailing end of the first fastener, and wherein the retainer region is relatively smaller in width to restrict removal of the first fastener from the one or more first openings.

18. The device of paragraph 1, wherein a first fastener and a first opening are configured such that the first fastener can engage and lock to the bone plate via the first opening.

19. The device of paragraph 18, wherein the first opening is configured such that the first fastener can lock to the bone plate within a range of angles.

20. The device of paragraph 19, wherein the first opening has a lip that engages a thread of the first fastener, and wherein the lip is deformable to accommodate the range of angles.

21. The device of paragraph 1, wherein the bone plate is thicker near the one or more first openings and near the at least one second opening relative to other regions of the bone plate.

22. A method of bone fixation, comprising:
disposing an intramedullary nail longitudinally in a medullary canal of a bone, the nail including a leading section and a trailing section and defining a long axis and also defining one or more transverse apertures in the trailing section;
placing one or more first fasteners into the bone and into the one or more transverse apertures;
coupling a bone plate to the nail by engaging a first plate portion of the bone plate with the one or more first fasteners; and
securing a second plate portion of the bone plate to the bone at a position more central along the bone than the first plate portion by placing one or more second fasteners through one or more openings of the second plate portion obliquely to the long axis and such that the one or more second fasteners extend adjacent and past the nail in a direction generally away from the leading section for engagement of another bone fragment.

23. The method of paragraph 22, further comprising a step of selecting an intramedullary nail including one or more fins disposed in the leading section of the nail.

24. The method of paragraph 23, further comprising a step of reaming the bone according to a longitudinal position of the one or more fins on the nail.

25. The method of paragraph 22, wherein the step of placing includes a step of placing at least two first fasteners into the bone and into at least two transverse apertures of the nail.

26. The method of paragraph 22, wherein the step of disposing includes a step of disposing an intramedullary nail longitudinally in a medullary canal of a femur.

27. The method of paragraph 26, wherein the step of disposing includes a step of introducing an intramedullary nail from a proximal end region of the femur.

28. The method of paragraph 22, wherein the step of placing is performed while one or more openings of the bone plate are aligned with the one or more transverse apertures of the nail.

29. The method of paragraph 22, wherein the step of placing includes a step of placing one or more first fasteners such that the one or more first fasteners extend through the one or more transverse apertures.

30. The method of paragraph 22, wherein the step of coupling includes a step of receiving the one or more first fasteners in one or more first openings of the first plate portion of the bone plate after the step of placing.

31. The method of paragraph 30, wherein the step of coupling includes a step of tilting the bone plate before the step of receiving such that the one or more first fasteners can be received in the one or more first openings of the first plate portion.

32. The method of paragraph 30, wherein the one or more first openings each include a receiver region of relatively larger width and a retainer region of relatively smaller width, wherein the step of receiving includes a step of receiving a first fastener in a respective receiver region, and wherein the step of coupling further includes a step of moving the bone plate such that the first fastener is disposed in the retainer region of its respective first opening.

33. The method of paragraph 22, wherein the step of coupling includes a step of locking the one or more first fasteners to the first plate portion of the bone plate.

34. The method of paragraph 33, wherein the step of locking the one or more first fasteners to the first plate portion of the bone plate includes a step of selecting, from a range of permitted angles, an angle at which each of the one or more first fasteners is to be locked with respect to the first plate portion.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

The invention claimed is:

1. A method of bone fixation, comprising:
placing an intramedullary nail proximally into a fractured femur;
disposing a buttress member proximally on the femur such that a first aperture and a second aperture of the buttress member are arranged at least generally along the femur from each other, with the second aperture more distally disposed than the first aperture;
placing a first fastener in the first aperture of the buttress member, into the femur, and through the nail such that the fastener is in threaded engagement with a pair of regions of the femur that are respectively disposed adjacent the buttress member and the nail and that are on opposite sides of the nail;
placing a second fastener in the second aperture of the buttress member and into the femur;
and placing a third fastener into a proximal region of the femur, the third fastener including a leading thread and a trailing thread, the leading thread having a greater pitch than the trailing thread and a fixed position relative to the trailing thread wherein the third fastener extends into a head of the femur and does not intersect the buttress member or the nail.

2. The method of claim 1, wherein the buttress member is a bone plate.

3. The method of claim 1, wherein the buttress member includes a rod region.

4. The method of claim 1, wherein the step of placing a third fastener applies compression to the femur.

5. The method of claim 1, wherein the third fastener extends posteriorly to the nail and includes a nonthreaded shaft extending between the leading thread and the trailing thread.

6. The method of claim 1, wherein a leading end of the third fastener is disposed more proximally in the femur than a leading end of the first fastener.

7. The method of claim 1, wherein the first fastener extends substantially orthogonally to a longitudinal axis defined by the nail, and wherein the third fastener extends obliquely to the longitudinal axis such that a leading end of the third fastener is disposed more proximally in the femur than a trailing end of the third fastener.

8. The method of claim 1, wherein the third fastener extends anteriorly to the nail with the leading thread disposed more proximally in the femur than the trailing thread.

9. The method of claim 8, wherein the third fastener includes a nonthreaded shaft disposed intermediate the leading thread and the trailing thread.

10. The method of claim 1, further comprising a step of placing another fastener longitudinally into the intramedullary nail from a trailing terminus thereof, into threaded engagement with the nail, and into engagement with the first fastener.

11. The method of claim 1, wherein the first fastener is placed in a first region of the buttress member and the second fastener in a second region of the buttress member, and wherein the buttress member extends continuously from the first region to the second region.

12. A method of bone fixation, comprising:
placing an intramedullary nail proximally into a fractured femur;
disposing a bone plate proximally on the femur;
placing a first fastener in a proximal aperture of the bone plate, into the femur, and through the nail such that the first fastener is in threaded engagement with a pair of regions of the femur that are respectively disposed adjacent the bone plate and the nail and that are on opposite sides of the nail;
placing a second fastener in a distal aperture of the bone plate and into the femur, without intersecting the nail; and
placing a third fastener into a head of the femur such that the third fastener does not intersect the bone plate or the nail,
wherein the third fastener includes a leading thread and a trailing thread of lesser pitch than the leading thread, wherein the leading thread and the trailing thread are fixed relative to each other and separated by a non-threaded region, and the third fastener is placed obliquely in the femur such that the leading thread is disposed more proximally in the femur than the trailing thread.

13. A method of bone fixation, comprising:
placing an intramedullary nail proximally into a fractured femur;
disposing a buttress member proximally on the femur; and
placing a fastener in an aperture of the buttress member, into the femur, and through the nail such that the fastener is in threaded engagement with a pair of regions of the femur that are respectively disposed adjacent the buttress member and the nail and that are on opposite sides of the nail; and
placing a pair of fasteners obliquely in the femur such that each fastener extends from a position distal of the aperture along the femur and into a head of the femur, each fastener of the pair including a leading thread and a trailing thread that has a smaller pitch and a fixed position relative to the leading thread.

14. The method of claim 13, wherein one fastener of the pair extends anteriorly of the nail and the other fastener of the pair extends posteriorly of the nail.

15. The method of claim 13, wherein at least one fastener of the pair does not intersect the buttress member.

\* \* \* \* \*